(12) United States Patent
Denu et al.

(10) Patent No.: US 9,988,665 B2
(45) Date of Patent: Jun. 5, 2018

(54) METHODS FOR DETERMINING PROTEIN BINDING SPECIFICITY USING PEPTIDE LIBRARIES

(75) Inventors: John M. Denu, McFarland, WI (US); Adam L. Garske, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 557 days.

(21) Appl. No.: 13/208,894

(22) Filed: Aug. 12, 2011

(65) Prior Publication Data

US 2012/0040860 A1 Feb. 16, 2012

Related U.S. Application Data

(63) Continuation of application No. 11/585,625, filed on Oct. 24, 2006, now Pat. No. 8,119,572.

(60) Provisional application No. 60/729,866, filed on Oct. 24, 2005.

(51) Int. Cl.
*C40B 40/10* (2006.01)
*C12Q 1/34* (2006.01)
*G01N 33/68* (2006.01)

(52) U.S. Cl.
CPC ............ *C12Q 1/34* (2013.01); *G01N 33/6845* (2013.01); *C40B 40/10* (2013.01); *G01N 2333/98* (2013.01)

(58) Field of Classification Search
None
See application file for complete search history.

(56) References Cited

U.S. PATENT DOCUMENTS

| | | |
|---|---|---|
| 5,510,240 A | 4/1996 | Lam et al. |
| 7,122,323 B2 | 10/2006 | Patek |
| 7,262,269 B2 | 8/2007 | Lam et al. |
| 2005/0069931 A1* | 3/2005 | Allis et al. ............... 435/6 |
| 2007/0160989 A1 | 7/2007 | Bawden et al. |
| 2009/0143240 A1 | 6/2009 | Harbison et al. |

OTHER PUBLICATIONS

Baxevanis, A.D. et al., "Histone sequence database: a compilation of highly-conserved nucleoprotein sequences," Nucleic Acids Research 24(1):245-247.
Marino-Ramirez, L. et al., "Histone structure and nucleosome stability," (2005) Expert Rev Proteomics 2(5):719-729.
Altschul et al., "Gapped BLAST and PSI-BLAST: A New Generation of Protein Database Search Programs", Nucl. Acids Res., 1997, 25(17):3389-3402.
Ausebel et al., 2001, Current Protocols in Molecular Biology, vols. 1-3, John Wiley & Sons, Inc.

(Continued)

*Primary Examiner* — Christian C Boesen
(74) *Attorney, Agent, or Firm* — Andrus Intellectual Property Law, LLP

(57) ABSTRACT

A method for determining protein binding specificity using a screen of a peptide library is provided. The method can be used to determine binding specificity for human $NAD^+$-dependent deacetylase SIRT1, and to identify the most efficiently deacetylated peptide sequences. The method can be also used to screen a combinatorial H4 histone N-terminal tail peptide library to examine the binding preferences of a α-phos (S1) H4 antibody toward all known possible H4 histone modification states.

11 Claims, 11 Drawing Sheets

(56) References Cited

OTHER PUBLICATIONS

Avalos et al., "Structure of a Sir2 Enzyme Bound to an Acetylates p53 Peptide", Mol. Cell., 2002, 10:523-535.
Blander et al., "SIRT1 Shows No Substrate Specificity in Vitro", J. Biol. Chem, 2005, 280(11):9780-9785.
Bodanszky, "Principles of Peptide Synthesis", 2nd Ed., 1976, 1993, Springer-Verlag, Germany.
Bodanszky et al., "Peptide Synthesis", 2nd Ed., 1976, John Wiley & Sons, Inc.
Borra et al., "Substrate Specificity and Kentic Mechanism of the Sir@ Family of NAD+-Dependent Histone/Protein Deacetylases", Biochemistry, 2004, 43:9877-9887.
Borra et al., "Mechanism of Human SIRT1 Activation by Resveratrol", J. Biol. Chem., 2005, 280(17):17187-17195.
Burgess et al., "Combinatorial Technologies Involving Reiterative Division/Coupling/Recombination: Statistical Considerations", Journal of Medicinal Chemistry, 1994, 37(19):2985-2987.
Carrillo et al., Science, 1975, 190:117-128.
Dieffenbach et al., PCR Primer: A Laboratory Manual, Cold Spring Harbor Laboratory Press, 1995.
Falciani et al., Bioactive Peptides from Libraries, Chem. & Biol., 2005, 12:417-426.
Furka et al., Int. J. Pept. Protein Res., 1991, 37:487-493.
Garske et al., "SIRT1 Top 40 Hits: Use of One-Bead, One-Compound Acetyl-Peptide Libraries and Quantum Dots to Probe Deacetylase Specificity", Biochemistry, 2006, 45:94-101.
Hu et al., "Determination of Substrate Specificity for Peptide Deformylase through the Screening of a combinatorial Peptide Library", Biochemistry, 1999, 38:643-650.
Jackson et al., "Mechanism of Nicotinamide Inhibition and Transglycosidation by Sir2 Histone/Protein Deacetylases", J. Biol. Chem., 2003, 278(51):50985-50998.
Karlin et al., "Methods for Assessing the Statistical Significance of Molecular Sequence Features by using General Scoring Schemes", Proc. Natl. Acad. Sci. USA, 1990, 87:2267-2268.
King et al., Int. J. Pept. Protein Res., 36:255-266.
Kodadek et al., "Optimized Protocols for the Isolation of Specific Protein-binding Peptides or Peptoids from Combinatorial Libraries Displayed on Beads", Mol. BioSyst., 2006, 2:25-35.
Kriegler, Gene Transfer and Expression: A Laboratory Manual, 1990, Stockton Press, New York.
Lam et al., "A New Type of Synthetic Peptide Library for Identifying Ligand-Binding Activity", Nature, 1991, 354:82-84.
Lam et al., "Applications of One-Bead One-Compound Combinatorial Libraries and Chemical Microarrays in Signal Transduction Research", Acc. Chem. Res., 2003, 36:370-377.
Nefzi et al., "Combinatorial Chemistry: Libraries from Libraries, The Art of the Diversity-Oriented Transformation of Resin-Bound Peptides and Chiral Polyamides to Low Molecular Weight Acyclic and Heterocyclic Compounds", J. Org. Chem., 2004, 69(11):3603-3609.
North et al., "The Human Sir2 Ortholog, SIRT2, is an NAD+-Dependent Tubulin Deacetylase", Mol. Cell., 2003, 11:437-444.
Olivos et al., Chembiochem, 2003, 4:1242-1245.
Sambrook et al., Molecular Cloning: A Laboratory Manual, 3rd Ed., 2000, Cold Spring Harbor Laboratory Press.
Songyang et al., "Use of an Oriented Peptide Library to Determine the Optimal Substrates of Protein Kinases", Curr. biol., 1994, 4(11):973-982.
Strahl et al., "The Language of Covalent Histone Modifications", Nature, 2000, 403:41-45.
Waterborg et al., Biochemistry, 1992, 31:6219-6223.
Youngquist et al., "Generation and Screening of Combinatorial Peptide Libraries Designed for Rapid Sequencing by Mass Spectrometry", J. Am. Chem. Soc., 1995, 117:3900-3906.
Zhao et al., "Structure of the Yeast Hst2 Protein Deacetylase in Ternary Complex with 2'-O-Acetyl ADP Ribose and Histone Peptide", Structure (Camb), 2003, 11:1403-1411.

* cited by examiner

METHODS FOR DETERMINING PROTEIN BINDING SPECIFICITY USING PEPTIDE LIBRARIES

CROSS-REFERENCE TO RELATED APPLICATIONS

This application is continuation of U.S. application Ser. No. 11/585,625, filed Oct. 24, 2006, which application was published on May 10, 2007, as U.S. Publication No. US2007/0105152, and claims priority to U.S. Provisional Patent Application Ser. No. 60/729,866, filed Oct. 24, 2005, the contents of which are incorporated herein by reference in their entireties.

SEQUENCE LISTING

This application includes an electronically submitted Sequence Listing in .txt format. The .txt file contains a sequence listing entitled "2015-10-21_5671-00037_ST25.txt" created on Oct. 21, 2015 and is 17,941 bytes in size. The Sequence Listing contained in this .txt file is part of the specification and is hereby incorporated by reference herein in its entirety.

GOVERNMENT INTERESTS

This invention was made with United States government support awarded by the NIH, grant Nos. GM065386 and GM059785. The United States government has certain rights in this invention.

FIELD OF THE INVENTION

This invention relates to a method for determining substrate specificity of protein binding using peptide libraries.

BACKGROUND OF THE INVENTION

An emerging paradigm for discovery in pharmaceutical and related biotechnology is the assembly of novel synthetic compound libraries by new methods of solid phase "combinatorial" synthesis. Combinatorial chemistry refers to a set of strategies for the parallel synthesis of multiple compounds or compounds mixtures, either in solution or on solid supports in the form of polymer-based resins ("beads").

One implementation of combinatorial synthesis that is suitable to produce large chemical libraries relies on "one-bead-one-compound" (OBOC) libraries, which contain from $10^6$ to $10^8$ compounds. These libraries are screened by performing a variety of chemical and biochemical assays to identify individual compounds eliciting a response. The chemical identity of such specific compounds can then be determined by direct analysis, using, e.g., micro-sequencing and mass spectrometry.

In peptidic OBOC libraries, peptide sequences from a group of selected amino-acid building blocks are represented in an on-bead format in which many copies of only one sequence exist on each bead. OBOC libraries permit sifting through a list of peptide substrate sequences to correlate top hits with protein sequence databases. This strategy has been used successfully, for example to determine the optimal peptide substrates of peptide deformylase, a $Fe^{2+}$ metalloenzyme that catalyzes N-terminal deformylation of nascent polypeptides in eubacteria (Hu et al., 1999, *Biochemistry* 38: 643-650).

Histone proteins serve to package DNA and to regulate its accessibility for processes including transcription, repair and replication. Six major histone classes are known. Two each of the class H2A, H2B, H3 and H4, assemble to form one nucleosome core particle around which DNA is wrapped. Acting as spools around which DNA winds, histones play a role in gene regulation. Histones achieve this control over DNA by acting as substrates to a host of posttranslational modifications that dictate function. Particularly dense with posttranslational information are the N-terminal histone tails. These can be covalently modified at several sites. Modifications of the histone tail include methylation, acetylation, phosphorylation, ubiquitination, sumoylation, citrullination, and ADP ribosylation. The core of the histones can also be modified. Combinations of modifications are thought to constitute a code, the so-called "histone code". The histone code hypothesis asserts that histone-binding proteins and histone-modifying enzymes read and interpret the post-translational states of properly "primed" histones to facilitate a particular outcome such as gene silencing, transcription, mitosis, etc. (Strahl et al., 2000, *Nature* 403: 41-45). However, thus far, the combinatorial complexity of the histone modification patterns has precluded a systematic inquiry of the patterns recognized by these "code readers", proteins and enzymes that would display preferential specificity for these context-dependent modifications.

Protein deacetylases have been implicated in a variety of disease states including aging, diabetes, HIV regulation, cancer, cardiovascular disorders, and neurodegenerative diseases. Histone deacetylase Inhibitors are currently in clinical trials as cancer treatments. In particular, the Silent information regulator 2 (Sir2) family of $NAD^+$ dependent protein deacetylases has been studied in recent years. This burgeoning interest can be attributed to the important roles of Sir2 enzymes (sirtuins) in regulating chromatin architecture, promoting transcriptional silencing and longevity, and in fatty acid metabolism. $NAD^+$ dependent lysyl deacetylation is characterized by the stoichiometric release of nicotinamide and a novel metabolite, O-acetyl-ADP-ribose (OAADPr).

The Sir2 family of deacetylases is highly conserved among all forms of life with seven known human homologs (SIRT1-7). The most studied mammalian homolog, SIRT1, is a nuclear enzyme that has been found to deacetylate a number of proteins. Histones H3 and H4, p53, p300, $TAF_168$, PCAF/MyoD, PGC-1alpha, FOXO1 and 4, NF-kappaB, and Tat are examples reported to be either biological targets and/or in vitro substrates of SIRT1. Collectively, the variety of proposed physiological targets reflects the functional diversity of SIRT1.

Identifying biological substrates is an important step in understanding the molecular basis for sirtuin phenotypes. However, in many of the studied cases, a certain degree of logical bias was used to link the target protein and SIRT1, as unbiased global substrate screening procedures were not used. Varying conclusions have been reached in regard to sirtuin substrate specificity and recognition. Most striking are the conclusions that sirtuins display minimal side-chain recognition (Avalos et al., 2002, *Mol. Cell.* 10: 523-535; Zhao et al., 2003, *Structure (Camb)* 11: 1403-1411) and that SIRT1 displays no substrate sequence specificity (Blander et al., 2005, *J. Biol. Chem.* 280: 9780-9785). In contrasting reports, clear substrate preferences were noted for yeast Sir2 and HST2 (Borra et al., 2004, *Biochemistry* 43: 9877-9887), and human SIRT2 (North et al., 2003, *Mol. Cell.* 11: 437-444).

To date, only one study has attempted to probe sirtuin substrate specificity using an acetyl-peptide library approach (Blander et al., 2005). Curiously, the study reported that SIRT1 displayed no substrate specificity in vitro, a conclusion based on an oriented peptide library. With this method, only globally preferred amino-acids could be resolved, and the actual sequence of individual peptides was not elucidated. Although the peptide library technique has been successful for examining protein kinase substrate specificity (Songyang at al., 1994, *Curr. Biol.* 4: 973-982), its usefulness toward protein deacetylases remains uncertain.

SUMMARY OF THE INVENTION

This invention provides a method for determining binding specificity of a protein deacetylase, which includes contacting the protein deacetylase with a peptide library. The peptide library includes a plurality of solid phase supports, where each solid phase support is linked to a different and distinct peptide. The method includes labeling the peptide library with a label specific for an amino group formed upon deacetylation, and correlating the label intensity with binding specificity of the protein deacetylase.

The label can be specific for an amino group formed upon deacetylation. The solid phase supports used to practice the method can be beads. The label can be colorimetric, radioactive, or fluorescent. The label can also be a labeled quantum dot.

The method can include sorting the solid phase supports from the labeled peptide library on the basis of label intensity. The method can include determining the sequence of the peptide attached to the solid phase support.

The protein deacetylase assayed by the method can be a sirtuin. Preferably, the protein deacetylase is SIRT1.

The peptide sequence can be selected from the group consisting of LNKDQ (SEQ ID NO: 26), WHKFQ (SEQ ID NO: 27), WHKFE (SEQ ID NO: 28), SYKQW (SEQ ID NO: 29), QPKQI (SEQ ID NO: 30), VQKII (SEQ ID NO: 31), HRKMP (SEQ ID NO: 32), HKKMP (SEQ ID NO: 33), AVKFM (SEQ ID NO: 34), NHKLL (SEQ ID NO: 35), RFKPE (SEQ ID NO: 36), KFKPE (SEQ ID NO: 37), FEKYR (SEQ ID NO: 38), MMKQQ (SEQ ID NO: 39), WGKSP (SEQ ID NO: 40), FEKYK (SEQ ID NO: 41), WPKWQ (SEQ ID NO: 42), RAKMD (SEQ ID NO: 43), KAKMD (SEQ ID NO: 44), GTKTG (SEQ ID NO: 45), GYKPT (SEQ ID NO: 46), IFKTF (SEQ ID NO: 47), TEKQE (SEQ ID NO: 48), HWKTH (SEQ ID NO: 49), DSKGA (SEQ ID NO: 50), SDKYH (SEQ ID NO: 51), NHKII (SEQ ID NO: 52), WWKHG (SEQ ID NO: 53), PIKEQ (SEQ ID NO: 54), RPKQF (SEQ ID NO: 55), KPKQF (SEQ ID NO: 56), DVKMH (SEQ ID NO: 57), IYKND (SEQ ID NO: 58), TPKNA (SEQ ID NO: 59), PGKLY (SEQ ID NO: 60), RWKIT (SEQ ID NO: 61), KWKIT (SEQ ID NO: 62), WRKIT (SEQ ID NO: 63), WKKIT (SEQ ID NO: 64), WPKIT (SEQ ID NO: 65), PWKIT (SEQ ID NO: 66), RPKSI (SEQ ID NO: 67), KPKSI (SEQ ID NO: 68), PRKSI (SEQ ID NO: 69), and PKKSI (SEQ ID NO: 70).

This invention provides a method for determining binding specificity of an enzyme. The method includes contacting a combinatorial peptide library with the enzyme, where the peptide library comprises a plurality of solid phase supports, where each solid phase support is linked to a different and distinct peptide, labeling peptides with a label specific for peptides covalently modified by the enzyme, and correlating the intensity of the label with peptides that are covalently modified by the enzyme, thereby determining binding specificity of the enzyme. The covalent modification may include a post-translational modification.

This invention provides an analytical method, which includes generating a combinatorial library of peptides that includes one or more peptide sequences attached to a solid phase support, where the combinatorial library includes a plurality of solid phase supports linked to a different and distinct peptide, and where each peptide comprises two or more chemically modified amino acids, contacting the combinatorial library with a protein, detecting the protein bound to one or more peptides using a label, and correlating the label intensity with peptides to which the protein binds, thereby determining the binding specificity of the protein. The solid phase supports can be beads. The label can be colorimetric, radioactive, or fluorescent. The label can be a labeled quantum dot. The solid phase supports from the labeled peptide library can be sorted on the basis of label intensity.

The method can include determining the sequence of the peptide attached to the solid phase support. The method can include determining the modification status of the peptide attached to the solid phase support.

Each peptide sequence can include at least 5 amino acids. At least one peptide sequence can include covalently modified amino acid.

The covalent modification can include methylation, acetylation, phosphorylation, ubiquitination, sumoylation, citrullination, or ADP ribosylation. The protein that is used to contact the combinatorial peptide library can be an enzyme. The protein that is used to contact the combinatorial peptide library can be an antibody. The combinatorial library can include one or more N-terminal peptide sequences from a histone.

corresponding to the first twenty-one amino acids of human histone H4 attached to a linker composed of two β-alanines (B) and a methionine (M).

Figure 11:
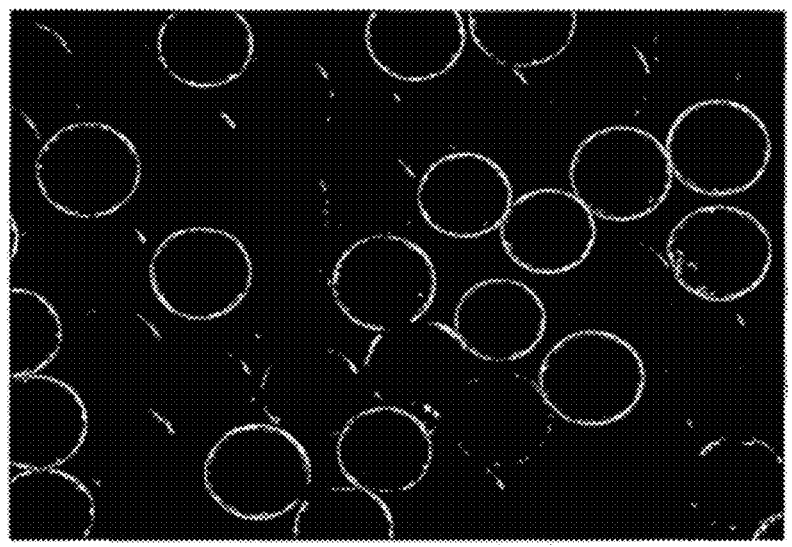

FIG. 11 is an image of a fluorescence micrograph showing the results of a H4 histone N-terminal tail library screen with a α-phos (S1) H4 antibody.

DETAILED DESCRIPTION OF THE INVENTION

The practice of the present invention employs, unless otherwise indicated, conventional techniques of peptide synthesis, molecular biology (including recombinant techniques), microbiology, cell biology, biochemistry, immunology, protein kinetics, and mass spectroscopy, which are within the skill of art. Such techniques are explained fully in the literature, e.g. in Bodanszky et al., 1976, Peptide Synthesis, $2^{nd}$ ed., John Wiley and Sons; Sambrook et al., 2000, *Molecular Cloning: A Laboratory Manual*, 3rd ed., Cold Spring Harbor Laboratory Press; *Current Protocols in Molecular Biology Volumes* 1-3, John Wiley & Sons, Inc.; Kriegler, 1990, *Gene Transfer and Expression: A Laboratory Manual*. Stockton Press, New York; Dieffenbach et al., 1995, *PCR Primer: A Laboratory Manual*, Cold Spring Harbor Laboratory Press, each of which is incorporated herein by reference in its entirety.

Generally, the nomenclature and the laboratory procedures in recombinant DNA technology described below are those well known and commonly employed in the art. Standard techniques are used for cloning, DNA and RNA isolation, amplification and purification. Generally, enzymatic reactions involving DNA ligase, DNA polymerase, restriction endonucleases and the like are performed according to the manufacturer's specifications. Procedures employing commercially available assay kits and reagents are typically used according to manufacturer-defined protocols unless otherwise noted.

The terms "a", "an", "the" and the like, unless otherwise indicated, include plural forms.

The term "acetyl", sometimes called "ethanoyl", is a functional group, the acyl of acetic acid, with chemical formula —$COCH_3$.

A "label" is a composition detectable by spectroscopic, photochemical, biochemical, immunochemical, or chemical means. For example, useful labels include $^{32}P$, fluorescent dyes, colorimetric labels, electron-dense reagents, enzymes (e.g., as commonly used in an ELISA), biotin, digoxigenin, or quantum dots. As used herein, the term "label" also includes indirect labeling of proteins using detectable labels bound to other molecules or complexes of molecules that bind to a protein of interest, including antibodies and proteins to which antisera or monoclonal antibodies specifically bind. As used herein, the term "colorimetric label" includes a label that is detected using an enzyme-linked assay.

"Antibodies" as used herein includes polyclonal and monoclonal antibodies, chimeric, and single chain antibodies, as well as Fab fragments, including the products of a Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A peptide or protein that is the predominant species present in a preparation is substantially purified. The term "purified" denotes that a peptide or protein gives rise to essentially one band in an electrophoretic gel or HPLC spectrum. Particularly, it means that the peptide or protein is at least 85% pure, more preferably at least 95% pure, and most preferably at least 99% pure.

Two peptides or polypeptides are said to be "identical" if the sequence of amino acid residues in the two sequences is the same when aligned for maximum correspondence as described below.

Peptide or protein sequence identities are evaluated using the Basic Local Alignment Search Tool ("BLAST") which is well known in the art (Karlin and Altschul, 1990, *Proc. Natl. Acad. Sci. USA* 87: 2267-2268; Altschul et al., 1997, *Nucl. Acids Res.* 25: 3389-3402). The BLAST programs can be used with the default parameters or with modified parameters provided by the user.

"Percentage of sequence identity" is determined by comparing two optimally aligned sequences over a comparison window, wherein the portion of the peptide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of amino acid sequences for purposes of this invention normally means peptide or polypeptide sequence identity of at least 40%. Preferred percent identity of peptides or polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 98.7%, or 99%.

Peptides or polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

The term "combinatorial library" refers to a collection of compounds synthesized in parallel or as a collection of compounds synthesized with mixtures of reagents or employing a split-and-mix methodology from a set of defined building blocks and using these building blocks in many combinations to generate a complex library of novel compounds. One implementation of combinatorial synthesis is the generation of "one-bead-one-compound" (OBOC) libraries, where each novel compound is represented on a single bead. These libraries can be screened by performing a variety of chemical and biochemical assays to identify individual compounds eliciting a response. The identity of the compound on the support is either known by prior knowledge from direct parallel synthetic procedures, or is determined by direct analysis after detection using, e.g., micro-sequencing and mass spectrometry.

In peptidic OBOC libraries, peptide from a group of selected amino-acid building blocks can be represented in an on-bead format in which many copies of only one sequence and of only one post-translationally modified state exist on each bead. Alternatively, peptides may be attached to other suitable types of support, including microarrays, microplates, chips, or other surfaces that are suitable for detecting protein binding events.

The invention described here uses both modified and unmodified amino acids as building blocks to create combinatorial peptide libraries to evaluate the binding specificities of proteins. These peptide libraries can vary in amino acid sequence and in modification state, e.g. methylation, acetylation or phosphorylation. The chemical identity (amino-acid sequence and post-translational status) of these peptides can be determined by direct analysis, using, e.g., micro-sequencing and mass spectrometry. Identification of the peptide sequences and their post-translational status can be performed before a protein binding assay is conducted. Alternatively, identification of the peptide sequences and their post-translational status can be performed before a protein binding assay is conducted. As well, identification of the peptide sequences and their post-translational status can be performed both before and after a protein binding assay is conducted.

The method includes screening a peptide library. In one example, the method provides for the use of a "one-bead-one-compound" (OBOC) peptide library, also known as OBOC combinatorial library. Examples of such libraries are described in Lam et al., 1991, *Nature* 354: 82-84, and in Furka et al., 1991, *Int. J. Pept. Protein Res*. 37: 487-493. The OBOC combinatorial library method synthesizes $10^2$-$10^8$ of random compounds such that each bead displays only one compound. Bead libraries are screened, and positive beads are isolated for structure analysis. Peptide substrates and inhibitors of protein kinases, and peptide ligands for cell surface receptors can be identified using this method (Lam et al., 2003, *Acc. Chem. Res*. 36: 370-377).

A peptide library can be synthesized on various types of solid supports using methods known in the art, for example those described in U.S. Pat. Nos. 7,122,323 and 5,510,240. Preferably, the library is synthesized using beads as solid phase support. In one example, the solid support can have the form of beaded resin ("beads").

The peptide library can be an OBOC acetyl-peptide library. One or more of the amino acids from the peptide can be deprotected using methods known in the art, e.g. trifluoroacetic acid. One or more of the amino acids from the peptide can be acetylated. In addition to acetylation of at least one amino acid, one or more of the amino acids can be modified in a variety of ways, for example through covalent modifications. Modifications can include post-translational modifications or introduction of non-classical amino acids, as described in U.S. Pat. No. 5,510,240.

The length of the peptide chain can vary. Preferably, the OBOC acetyl-peptide library is generated using 5-mer peptides, i.e. peptides with 5 amino acid residues. One or more of these 5 amino acids from the peptide can be acetylated. Preferably, the central (third) amino acid is acetylated. More preferably, the central, acetylated amino acid is lysine. Preferably, unique sequences are constructed around a central epsilon-amino acetylated lysine.

When the peptide library is an acetyl-peptide library, the method can be used for determining protein deacetylase substrate specificity. The protein deacetylase can belong to the sirtuin family. Preferably, the protein deacetylase is SIRT1.

The peptide library can be a combinatorial peptide library based on N-terminal histone sequences. In this example, one or more of the peptide sequences include N-terminal histone sequences. Preferably, the combinatorial OBOC peptide library is based on N-terminal amino acid sequence of histone H4. The N-terminal histone sequences can have a different number of amino acid residues. Preferably, the N-terminal histone sequences are 21-mers, i.e. they have 21 amino acid residues. These sequences can be attached to solid support directly, or via one or more amino acids that act as linkers.

The N-terminal histone sequences can be modified to include various post-translational modifications. The modifications can be covalent. The modifications can include, for example, methylation, acetylation, phosphorylation, ubiquitination, sumoylation, citrullination, or ADP ribosylation. Modifications can also include the introduction of non-classical amino acids. Each N-terminal histone sequence can include one or more of these modifications.

When the combinatorial peptide library is based on N-terminal histone sequences, the invention provides methods for determining and evaluating histone-binding proteins or histone-modifying enzymes. Preferably, the histone-binding protein is an antibody. More preferably, the histone-binding protein is an α-phos (S1) H4 antibody.

Prior to library construction, peptide length may initially be considered to determine whether relatively short peptides would function as efficient protein substrates. For example, prior to library construction, peptide length may be considered to determine whether relatively short acetyl-peptides would function as efficient enzymatic substrates. Also, for example, prior to library construction, peptide length may be considered to determine the preferred length of the N-terminal amino acid chain of a histone and its efficiency as a protein substrate.

The method provides for the use of a quantum dot tagging, i.e. labeling strategy. Quantum dots are nanoparticles that exhibit exquisite photochemical properties owing to their semiconductor cores and are emerging as ideal fluorophores for screening OBOC libraries (Falciani of al., 2005, *Chem. Biol*. 12: 417-426). These properties include robust photostability, high quantum yield, and a sharp emission with a broad range of excitation wavelengths. Coupled with a bead-sorting instrument, quantum dots allow the screening of hundreds of thousands of peptide sequences for protein binding and protein activity in a single day. Quantum dots can be used, for example, to label the protein that is in contact with a peptide that is attached to a bead.

The method provides for sorting of beads. Bead sorting can be performed manually or it can be automated. Bead sorting is preferably performed based on beads that are labeled. Bead labeling can be performed using a variety of methods known in the art. Preferably, beads can be labeled with a fluorescent label or with any other type of label. When beads are labeled with a fluorescent label, then the method can include fluorescent bead-sorting. In one example, a protein that is assayed and that specifically binds to beads, can be labeled. In another example, beads with peptides deacetylated by a protein deacetylase can be labeled. For example, these beads can be first biotinylated and then tagged (labeled) with streptavidin-coated quantum dots.

After bead-sorting, peptides sequences and their corresponding post-translationally-modified status can be extracted from individual beads in the library. The sequences and modification state of these peptides can then be identified. Identification of the peptides can be performed, for example, by mass spectrometry, or by micro-sequencing. Identification of the peptides can thus identify the particular sequences and modification state for which the assayed protein shows considerable binding preference.

A peptide library that is already spatially-addressed, e.g. each sequence and modification state is known at each support (e.g. bead), can be screened by the methods described.

The present invention provides a high-throughput method for determining substrate specificity of protein deacetylases using a one-bead, one-compound OBOC acetyl-peptide library with a quantum dot tagging strategy and automated bead-sorting. The OBOC acetyl-peptide library method allows context-specific identification of preferred peptide substrates. This is in contrast to the previously published approach that can only uncover globally-preferred amino-acids at each position. The OBOC acetyl-peptide library method can be applied to any histone/protein deacetylase from class I, II or III.

Various applications of peptide libraries of this type can be envisioned. For example, the sequence information obtained from this library can be used to generate acetyl-peptide specific antibodies for Western blot analysis. This can provide in vivo validation of acetylation at protein acetylation sites discovered in BLAST searches and sequence comparisons. Such antibodies could also be employed in immunoprecipitation studies. Mass spectral analysis could then be performed to identify the acetylated proteins. Identification of enzymatic substrates, i.e. the sequence information obtained from the library, can also be used to generate acetyl-peptide specific inhibitors.

Other uses of the library include the creation of super-substrates for the in vivo generation of O-acetyl-ADP-ribose (OAADPr) to elucidate its cellular roles. Co-crystal studies could be executed to uncover how Sir2 interacts with these optimal substrate sequences. Limited peptide substrates co-crystallized with Sir2 have shown interactions primarily with the peptide backbone (Avalos et al., 2002, *Mol. Cell.* 10: 523-535). However, the method of this invention provides for the use of side-chain interactions to bind and catalyze protein deacetylation.

Hits from libraries of this type could serve as starting points for the design of peptidomimetics for a variety of applications, e.g. for use as potential therapeutics (Nefzi et al., 2004, *J. Org. Chem.* 69: 3603-3609; Falciani et al., 2005, *Chem. Biol.* 12: 417-426). Optimized substrates reflect higher binding affinity to a protein, e.g. enzyme. Modification of the peptide to prohibit enzymatic turnover and protease degradation could be implemented to generate a specific, tight-binding in vivo inhibitor.

The original peptide sequences can be further modified to confer altered chemical and biological properties (Nefzi et al., 2004, *J. Org. Chem.* 69: 3603-3609; Falciani et al., 2005, *Chem. Biol.* 12: 417-426). This strategy has been used to tailor-make peptides into therapeutics that avoid the pitfalls of proteolytic cleavage, rapid clearance from the circulatory system, inability to pass through the blood brain barrier, and lack of oral activity (Nefzi at al., 2004).

This invention provides a method for identification of the molecular recognition events involved in the histone code via OBOC combinatorial peptide libraries based on N-terminal histone sequences. This method provides for synthesis and evaluation of all possible permutations (at known modification sites) of the 21 N-terminal amino acids of histone H4. In a preferred embodiment, the evaluation of the binding specificity is performed using an antibody directed to serine phosphorylation and a quantum dot detection strategy (Garske and Denu, 2006, *Biochemistry* 45: 94-101; Kodadek et al., 2006, *Mol. Biosyst.* 2: 25-35). However, the general approach is applicable to interrogating the preferences of any histone-binding protein or any histone-modifying enzyme. As well, this approach may find use in histone-specific antibody screening.

The following examples are offered to illustrate, but not to limit the claimed invention.

Example 1. Use of a One-Bead-One-Compound Peptide Library to Identify Deacetylase Specificity General All amino acid derivatives and resins were purchased from Peptides International (Louisville, Ky.) or from Bachem (Bubendorf, Switzerland). Peptides used in the solution deacetylase assays were obtained from the University of Wisconsin-Madison Biotechnology Core Facility. Other chemical reagents were obtained from Sigma-Aldrich (St. Louis, Mo.), Acros (Geel, Belgium), Novabiochem (San Diego, Calif.), Amersham Biosciences (Buckinghamshire, England), or Quantum Dot (Hayward, Calif.). Reaction vessels for peptide library synthesis were purchased from Alltech Chromatography (Deerfield, Ill.).

Analytical gradient HPLC was conducted on a Shimadzu series 2010C HPLC with a Vydac C18 column (10 μm, 4.6×250 mm). All runs used linear gradients of 0.05% aqueous TFA and 0.02% TFA in acetonitrile. MALDI-TOF MS was performed on a Bruker REFLEX II using α-cyano-4-hydroxy-cinnamic acid as matrix. Fluorescent bead sorting was carried out on a COPAS Select (Union Biometrica, Holliston, Mass.) instrument. Fluorescence microscopy was done on an Olympus IX81 instrument (Tokyo, Japan) equipped with a Hamamatsu digital camera (Hamamatsu-City, Japan).

SIRT1, SIRT2, and ySir2 were expressed and purified as previously described (Borra et al., 2004, *Biochemistry* 43: 9877-9887; Borra of al., 2005, *J. Biol. Chem.* 280: 17187-17195).

Prior to kinetic analysis, peptide concentrations were established by amino acid analysis (AAA) or by a coupled assay in which $NAD^+$ leftover from exhaustive deacetylation reactions (acetylated peptide was typically incubated with 5-10 μM Sir2 and 80 μM $NAD^+$ for 20 min) was quantitatively converted to NADH with alcohol dehydrogenase and monitored spectrophotometrically in real-time at 340 nm. Peptide concentrations were obtained by subtracting the amount of NADH formed from the original amount of $NAD^+$ used in the reaction.

Solution Deacetylation Assays

All solution phase Sir2 assays were carried out at 25° C. in 50 mM Tris.HCl. Reactions were done in 50-100 μL with 0.1-1.5 μM enzyme, 0.1-1.2 mM $NAD^+$, 0.5-1000 μM peptide and 1 mM DTT. Reaction mixtures were quenched with TFA to a final concentration of 1% after 5-10 min and nicotinamide levels were quantitated by HPLC at 264 nm.

Alternatively, $[^{32}P]$-$NAD^+$ (10 mCi/mL) was used in assays and quenched reaction mixtures were spotted on a silica TLC plate and run in a chamber containing 60% ethanol and 40 2.5 mM ammonium acetate for 3-4 hours. Levels of $^{32}$P-OAADPr and $^{32}$P-NAD$^+$ were then quantitated by phosphorimaging and the fraction turnover was calculated. Saturation curves were done at varying concentrations of peptide while holding that of NAD$^+$ constant. Time points were chosen such that product formation never exceeded 20% conversion and data were plotted as rate (s$^{-1}$) vs. peptide concentration. Plots were fitted to the Michaelis-Menten equation, $v=[(k_{cat}/K_m)[S]]/(1+[S]/K_m)$ using Kaleidagraph software (Reading, Pa.) to extract $K_m$ and $k_{cat}/K_m$.

Screening Methodology

The screening strategy used the reaction of biotin N-hydroxy-succinimide ester with the newly generated ε-amino group formed upon SIRT1 deacetylation. Subsequent binding of the streptavidin conjugated quantum dots provided the fluorescent tag for screening.

Initially, it was established that quantum dot labeling was proportional to the molar abundance of reacted biotin. Resin bearing free amino groups were aliquoted into five reaction vessels and labeled with 1, 0.5, 0.01, 0.001 and 0 equivalents of biotin N-hydroxy-succinimide ester. After differential labeling, the resin was pooled into reaction vessel and a streptavidin conjugated quantum dot ($\lambda_{em}$=605 nm) solution was added. After draining the quantum dot solution and washing the resin, the resulting pooled beads displayed differential levels of associated quantum dots, correlating with the amount of covalently linked biotin.

Figure 1:
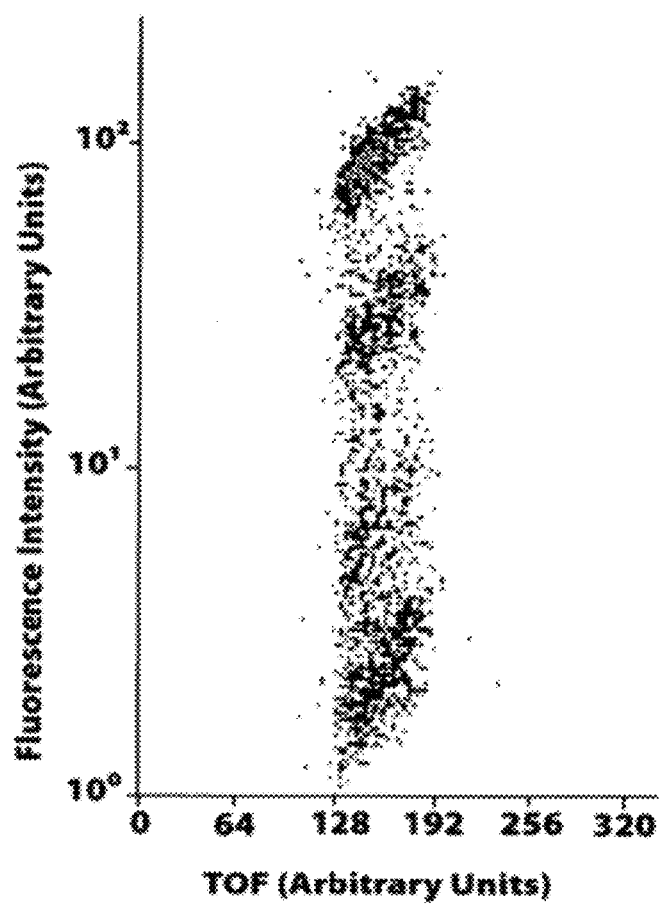
FIG. 1 is a graph showing data from differential biotinylation experiments with quantum dot tagging.

To provide a quantitative assessment of fluorescent quantum dot labeling, a complex object parametric analyzer and sorter (COPAS) instrument was utilized. COPAS sorts beads based on fluorescence intensity while also gathering data on bead size (time of flight). Using this instrument, beads labeled in the previously mentioned experiment were sorted with an excitation of 488 nm and an emission of 610 nm. The fluorescence distribution was plotted and distinct populations could be visualized (FIG. 1). FIG. 1 depicts a log scale plot of fluorescence intensity vs. TOF (bead size) for quantum dot labeled beads with biotinylation levels of 1, 0.5, 0.01, 0.001 and 0 equivalents as analyzed by the COPAS beadsorter at 610 nm.

These populations resided in a fluorescence regime that encompassed more than two orders of magnitude. Moreover, the bead groupings corresponded to the differential levels of biotinylation (although the 0.001 and 0 biotin equivalents coalesced into a single cluster). When the emission wavelength was set to green light ($\lambda_{ex}$=510 nm) corresponding to the intrinsic TentaGel autofluorescence, only a single population was observed. Quantum dot labeling was found to be quantitative in sub-stoichiometric amounts. It can be coupled to a sorting instrument such as the COPAS instrument for sorting beads on the basis of fluorescence intensity.

Figure 2:
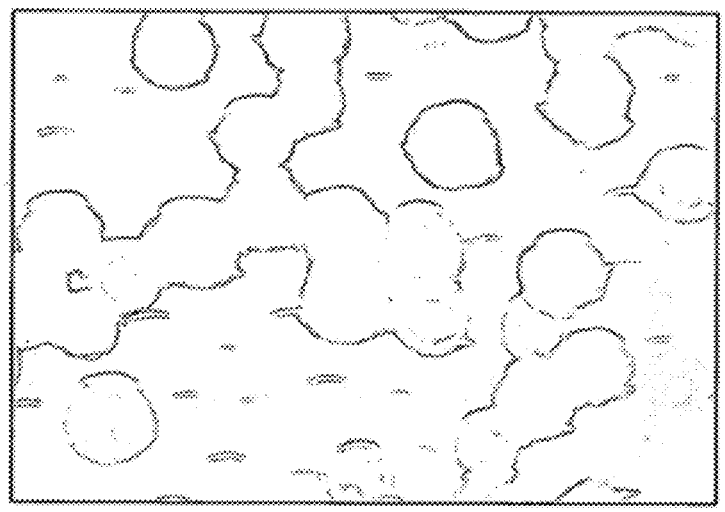
FIG. 2 is an image of a fluorescence micrograph showing data from differential biotinylation experiments with quantum dot tagging.

FIG. 2 depicts a microscopic representation of the differentially biotinylated TentaGel beads after incubation with streptavidin coated quantum dots. Quantum dot labeled beads appear white (orange/red in original) while TentaGel autofluorescence is gray (green in original). The varying shades of brightness (orange in original) correlated qualitatively to the amount of bound quantum dot.

Library Design

Prior to library construction, it was essential to determine whether relatively short acetyl-peptides would function as efficient substrates of Sir2 enzymes. To evaluate peptide length requirements, 10 acetyl-lysine containing peptides corresponding to the histone H3 sequence surrounding Lys-14 and of varying length were assayed using SIRT1 and a variety of other sirtuins (SIRT2; yeast Sir2, ySir2; and *Trypanosoma brucei* Sir2, TbSir2). Deacetylation assays were conducted at fixed NAD$^+$ concentrations while peptide concentrations were varied to produce saturation curves. The resulting data were fitted to the Michaelis-Menten equation to yield catalytic efficiencies, as defined by the apparent second order rate constant ($k_{cat}/K_m$), which takes into consideration both binding and catalysis. All peptides used in these studies were N-terminally acetylated, but the N-terminus was not deacetylated by sirtuins in control assays.

The results, shown in Table 1, are represented as relative $k_{cat}/K_m$ values, with the longest peptide AcTGG(AcK)APRK (SEQ ID NO: 9) given a value of one. In these studies, all sirtuins surveyed showed no more than a 2 to 3-fold difference in $k_{cat}/K_m$ for the various peptide substrates. Thus, the shortest peptide, a 5-mer, was similar in catalytic efficiency to the longest peptides in this preliminary set, regardless of the enzyme assayed. These observations suggest amino acids beyond the -2 and +2 positions are not necessary for efficient binding and catalysis by sirtuins. For library construction, balancing minimal peptide length with practical limitations of library complexity were important considerations. Consequently, a 5-mer library with an acetylated lysine residue in the central position was constructed.

TABLE 1

Summary of the relative catalytic efficiencies ($k_{cat}/K_m$) of various Sir2 homologs with ten peptide substrates

| | Peptide | Relative $k_{cat}/K_m$ | | | |
|---|---|---|---|---|---|
| | | SIRT1 | SIRT2 | ySir2 | TbSir2 |
| SEQ ID NO: 3 | AcGG(AcK)AP | 1.72 ± 0.48 | 0.56 ± 0.07 | 1.51 ± 0.69 | 1.27 ± 0.16 |
| SEQ ID NO: 4 | AcTGG(AcK)AP | 0.54 ± 0.11 | 0.55 ± 0.07 | 1.62 ± 0.62 | 0.74 ± 0.18 |
| SEQ ID NO: 5 | AcSTGG(AcK)AP | 1.61 ± 0.46 | 0.78 ± 0.09 | 1.83 ± 0.83 | 0.59 ± 0.12 |
| SEQ ID NO: 6 | AcGG(AcK)APR | 0.68 ± 0.12 | 0.60 ± 0.10 | 2.53 ± 1.29 | 1.18 ± 0.22 |
| SEQ ID NO: 7 | AcTGG(AcK)APR | 0.64 ± 0.10 | 0.72 ± 0.09 | 1.72 ± 0.81 | 0.89 ± 0.23 |
| SEQ ID NO: 8 | AcSTGG(AcK)APR | 0.67 ± 0.10 | 0.93 ± 0.20 | 1.60 ± 0.79 | 1.39 ± 0.16 |
| SEQ ID NO: 9 | AcGG(AcK)APRK | 1.01 ± 0.18 | 0.68 ± 0.10 | 2.33 ± 0.93 | 1.82 ± 0.23 |

TABLE 1-continued

Summary of the relative catalytic efficiencies ($k_{cat}/K_m$) of various Sir2 homologs with ten peptide substrates

| | | Relative $k_{cat}/K_m$ | | | |
|---|---|---|---|---|---|
| | Peptide | SIRT1 | SIRT2 | ySir2 | TbSir2 |
| SEQ ID NO: 10 | AcGG(AcK)APRKQ | 0.80 ± 0.21 | 0.66 ± 0.09 | 2.09 ± 0.79 | 1.43 ± 0.20 |
| SEQ ID NO: 11 | AcKSTGG(AcK)AP | 0.71 ± 0.11 | 0.59 ± 0.10 | 2.12 ± 0.81 | 1.81 ± 0.69 |
| SEQ ID NO: 12 | AcTGG(AcK)APRK | 1.00 ± 0.08 | 1.00 ± 0.09 | 1.00 ± 0.36 | 1.00 ± 0.09 |

Library Construction

After validating that quantitative quantum dot labeling could be used in conjunction with fluorescence-based bead sorting, an OBOC peptide library was constructed using the split-pool method (Lam et al., 1991, *Nature* 354: 82-84; Furka et al., 1991, *Int. J. Pept. Protein Res.* 37: 487-493). Eighteen variable amino acids were used at four positions centered around an acetylated lysine (two amino acids on each side of the acetylated lysine residue). All common natural amino acids excluding cysteine, lysine, methionine and arginine were used. To mimic charged residues, dimethyl arginine was substituted for lysine and arginine. To avoid unwanted cyanogen bromide cleavage points, isosteric norleucine was used in place of methionine. Lysine and cysteine were not included in the library because both residues would produce false hits (in addition to the problems posed by disulfide formation in the latter case) because the nucleophilicity of the amine and sulfhydryl groups respectively would result in their biotinylation and subsequent quantum dot labeling.

The acetylated peptide library was constructed on Tenta-Gel Macrobead $NH_2$ resin (280-320 μm, 0.21 mmol/g loading, 65,550 beads/g) using the split-pool approach. Fmoc/tBu methodology (Bodanszky, 1993, *Principles of Peptide Synthesis,* 2nd ed., Springer-Verlag, Germany) was used to carry out the library synthesis on 4.80 g of resin. Prior to randomization, a four amino acid linker, BBRM (B=β-alanine) was synthesized. After deprotecting the N-terminus with 20% (v/v) piperidine in DMF for 15 min, the resin was split equally into eighteen separate reaction vessels (one for each amino acid in the library). Four equivalents of amino acid and coupling reagent in addition to 5% (mol/mol) capping reagent were added to each vessel for later sequencing.

Figure 3:
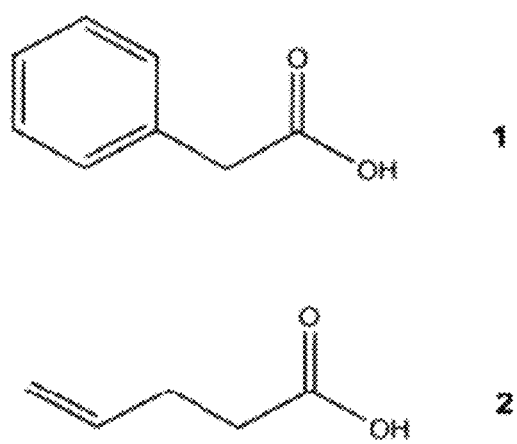
FIG. 3 depicts parts of the capping scheme used for the identification of randomized peptide sequences: (1, top) chemical structure of the capping reagent phenylacetic acid; (2, bottom) chemical structure of the capping reagent pentenoic acid.
Figure 4:
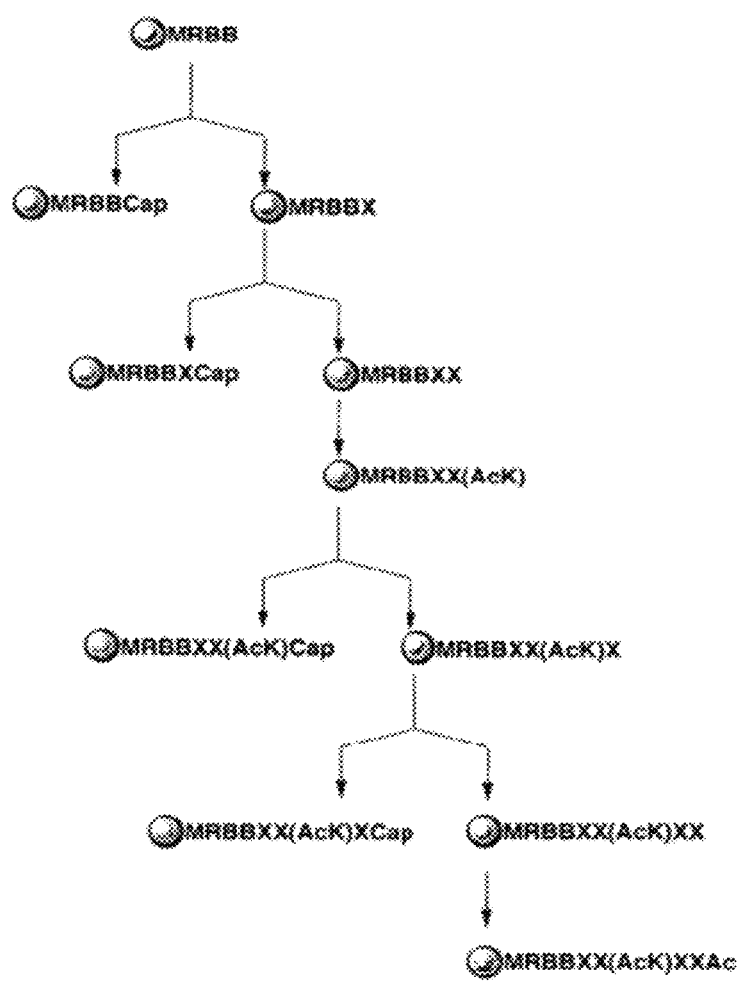
FIG. 4 illustrates the capping strategy used during peptide synthesis for generation of a peptidic "mass ladder".

Capping reagents included phenylacetic acid and 4-pentenoic acid (FIG. 3). Phenylacetic acid was used in conjunction with norleucine, while 4-pentenoic acid was used with all other amino acids. Equimolar ratios of both capping reagents were used for isoleucine, asparagine, glutamine and histidine. After a second coupling, the resin from all vessels was washed three times each with DCM and DMF, pooled and deprotected. Next, the resin was redistributed into the reaction vessels for coupling of the second randomized residue. The process was repeated and after pooling, N-ε-acetyl lysine was installed as the third residue with no capping (FIG. 4). The split-pool technique was repeated for the fourth and fifth randomized residues. After the final N-terminal deprotection, the N-termini of all the peptides were acetylated (70% DCM, 25% acetic anhydride, 5% triethylamine) and washed with DCM. Reagent K (TFA/EDT/thioanisole/water/phenol: 82.5%, 2.5%, 5%, 5%, 5%) (King et al., *Int. J. Pept. Protein Res.* 36: 255-266) was used as the global deprotection cocktail. The resin was washed thoroughly with DCM and stored at −20° C. until use.

In preliminary studies, incorporation of arginine residues beyond the linker position gave false positive signals in the on-bead assays, due to reaction with the biotin ester during the labeling step. This was an unfortunate result, as it precluded incorporation of arginine in the library. The same problems posed by the reactivity of arginine have prevented its incorporation in a previous library (Hu et al., 1999, *Biochemistry* 38: 643-650). To mimic positively charged residues, lysine and arginine, symmetrical dimethyl arginine was used. Thus, $18^4$=104,907 sequences were represented in the library. A threefold excess of beads was used to give 95% probability that all sequences were represented (Altschul et al., 1997, *Nucl. Acids Res.* 25: 3389-3402).

Figure 5:
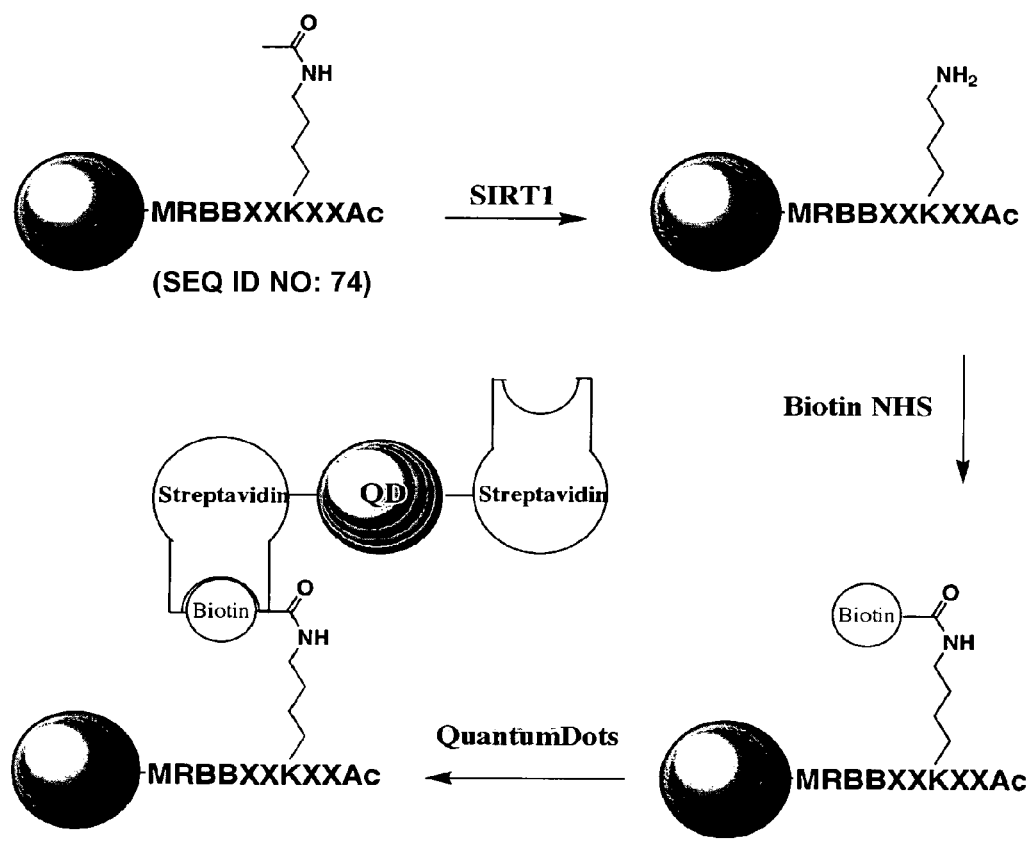
FIG. 5 schematically depicts a quantum dot bead-based assay.

After library synthesis, the on-bead SIRT1 deacetylation assay was carried out, as shown in FIG. 5. In this assay, all beads were simultaneously subjected to deacetylation conditions (0.35 μM SIRT1, 12 min at 25° C.), allowing competition of all peptide sequences for reaction with SIRT1. Afterwards, the beads were washed and subjected to biotinylation conditions in DMF. Excess reagent was removed prior to blocking non-specific protein binding sites with BSA and subsequent quantum dot labeling. Lastly, beads were washed a final time and sorted using a COPAS instrument to obtain data such as those shown in FIG. 6.

Figure 6:
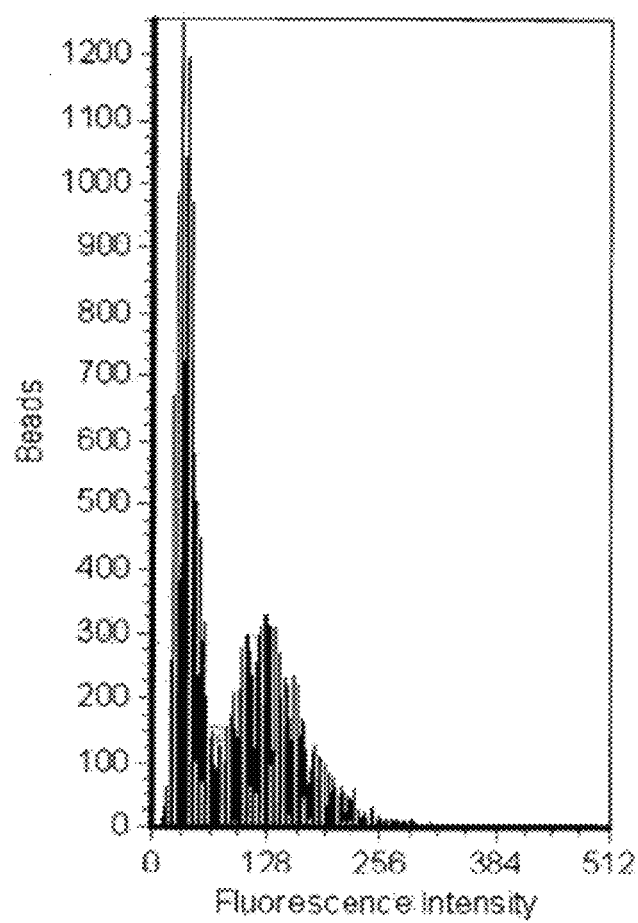
FIG. 6 is a graph showing the fluorescence distribution of library members.

FIG. 6 shows an example of the fluorescence distribution of library members. The histogram displays the number of beads versus fluorescence intensity of a portion of the library. Note that the sharp peak on the left corresponds to bubbles trapped in the instrument.

Figure 7:
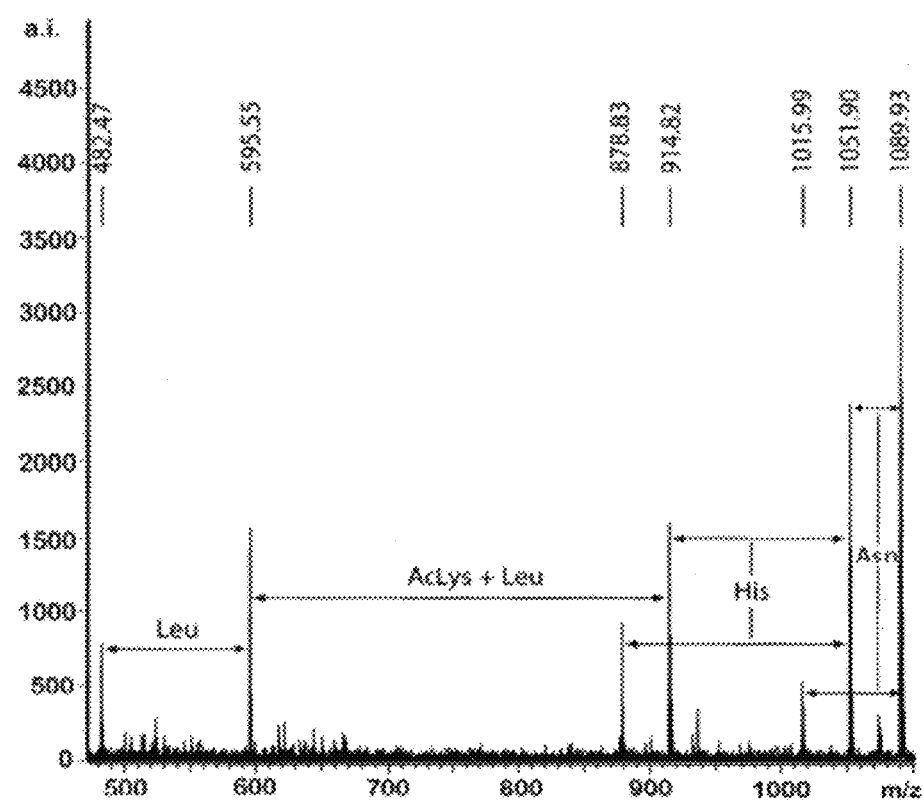
FIG. 7 is a graph showing the mass spectrum obtained for microsequencing of a top hit peptide sequence.

FIG. 7 shows a representative mass spectrum obtained from microsequencing of the cleavage products of one of the top forty most fluorescent beads (top hit sequence). The amino acids corresponding to various mass differences are annotated. Signature doublets are obtained for asparagine and histidine as result of the use of both capping reagents (1 and 2; see FIG. 3) during those coupling reactions.

Determining the viability of quantitative quantum dot analysis was also performed. Five 10 mg portions of Tenta-Gel S $NH_2$ resin (90 μm, 0.26 mmol/g loading, 2.86×$10^6$ beads/g) were divided out and swollen in DCM. After washing with DCM (3×1 mL) and DMF (3×1 mL), the beads were labeled with 1, 0.5, 0.01 and 0.001 molar equivalents of N-hydroxysuccinimidobiotin in 200 μL portions of DMF. After an hour of rocking at room temperature, the solutions were drained and washed with DMF (3×1 mL). Approximately 5 mg of resin from each of the above reactions were combined and incubated with 1 mL BSA (1 mg/mL) in TBST buffer (25 mM Tris.HCl, pH 8.0, 150 mM NaCl, and 0.1% Tween 20) for 1 hour. The resin was washed with TBST buffer (3×1 mL) and drained to the level of the resin bed. At this point, 500 μL of 75 nM streptavidin coated Q-dot 605 in TBST buffer was poured over the resin and rocked for 2 hours, after which the solution was drained to the resin bed before washing with TBST (10×1 mL). Beads were photographed using a fluorescence microscope with a FITC filter and sorted on the basis of fluorescence ($\lambda_{ex}$=488 nm, $\lambda_{em}$=610 nm) with a COPAS Select sorting instrument. Sorting data were evaluated with FCS Express (De Novo Software, Thornhill, Ontario) in histogram and dot plot form.

On-Bead Peptide Library Deacetylation by SIRT1

The entire library was assayed in a 75-mL column equipped with a filter. Prior to the assay, the resin was sequentially washed with DCM (3×50 mL), DMF (3×50 mL) and deacetylation assay buffer (50 mM Tris, pH 7.5) (1×50 mL). The enzymatic reaction was initiated upon addition of 50 mL of deacetylation cocktail (0.35 µM SIRT1, 1.5 mM β-NAD⁺, 1 mM DTT). The reaction mixture was allowed to rock gently for 12 min. After draining, the resin was washed with doubly distilled water (5×50 mL) and DMF (5×50 mL). Afterwards, the resin was rocked with biotin N-hydroxy-succinimide ester in DMF (3.5 mM, 50 mL) for 20 min. The solution was drained and the resin was washed with DMF (6×50 mL) and TBST buffer (2×50 mL).

To reduce nonspecific binding, the beads were incubated with 50 mL of BSA (2 mg/mL) in TBST buffer for 1.5 hours. After draining and washing with TBST buffer (1×50 mL), 50 mL of 4 nM streptavidin coated Q-Dot 605 in TBST buffer was added and the mixture was allowed to rock for 2 hours. Again, the solution was drained and washed with TBST buffer (10×50 mL). The resin was then suspended in a minimal amount of TBST buffer and refrigerated at 4° C. overnight.

Strategy for Sequencing Peptides on Beads

In order to extract peptide sequences from individual beads in the library, a previously developed capping method was improved, in which sequence decoding is done by reading a mass spectral peptide ladder (Youngquist et al., 1995, *J. Am. Chem. Soc.* 117: 3900-3906). Instead of using the acetyl group for capping during peptide synthesis, two carboxylic acids were used: phenylacetic acid (1) and 4-pentenoic acid (2) (FIG. 3). First, a four amino acid linker was synthesized onto TentaGel beads to extend the bound peptide into solution and to bring the peptide mass out of the MALDI matrix region. This linker was composed of methionine (for a cyanogen bromide cleavage point), arginine (for improved mass spectral analysis) and two β-alanines (for added flexibility). This capping method, which utilizes two caps, allows for the identification of up to three isobaric (i.e., – of identical mass) amino acids.

In each coupling step of a randomized residue, a small amount of capping reagent was added to terminate chain growth for later sequencing (FIG. 4). In each capping step, either one or both of the capping reagents were used. The use of two reagents assisted in deciphering amino acids of similar or identical masses. In cases, where both caps were used, a signature doublet would appear on the mass spectrum. By HPLC analysis, it was determined that 5 mol % capping at each step in the synthesis of a prototypical 5-mer yielded ~79% full-length peptide. This amount of capping reagent provided a more than adequate amount for on-bead assay, yet produced enough capped material to produce quality peptide ladders in the mass spectra. An acetyl group served as the N-terminal cap.

Library Screening

Beads were sorted on the basis of fluorescence ($\lambda_{ex}$=488 nm, $\lambda_{em}$=610 nm) using the COPAS instrument. Initially, the 300 most intensely fluorescent beads (0.1%) were collected, pooled and then sorted a second time to generate an enriched sample of the 45 brightest beads. After washing in a guanidinium hydrochloride solution, single beads were placed in separate microcentrifuge tubes and treated overnight with a cyanogen bromide cleavage cocktail. The cleavage products were subsequently subjected to MALDI-TOF MS for sequence analysis (FIG. 7). Of those 45 beads, 33 were sequenced successfully from their mass spectra (Table 2), 6 were found to be damaged and were not sequenced, while the remaining 6 yielded spectra that were not interpretable. BLAST searches of the mammalian proteome were performed in the short, nearly exact mode for the 33 sequences obtained from the library (see Table 4).

Shown in Table 2 are peptide sequences of hits from the SIRT1 combinatorial library screen. Position −2 is the N-terminal end and Position +2 is the C-terminal end. Uncertainty in the order of N-terminal (and adjacent) amino acids is signified by the symbol /.

TABLE 2

Peptide sequences of hits from the SIRT1 combinatorial library screen

| Sequence Identifiers | Position −2 | Position −1 | Position 0 | Position +1 | Position +2 |
|---|---|---|---|---|---|
| SEQ ID NO: 26 | Leu | Asn | AcLys | Asp | Gln |
| SEQ ID NO: 27 | Trp | His | AcLys | Phe | Gln |
| SEQ ID NO: 28 | Trp | His | AcLys | Phe | Glu |
| SEQ ID NO: 29 | Ser | Tyr | AcLys | Gln | Trp |
| SEQ ID NO: 30 | Gln | Pro | AcLys | Gln | Ile |
| SEQ ID NO: 31 | Val | Gln | AcLys | Ile | Ile |
| SEQ ID NO: 32/33 | His | Me₂Arg | AcLys | Nle | Pro |
| SEQ ID NO: 34 | Ala | Val | AcLys | Phe | Nle |
| SEQ ID NO: 35 | Asn | His | AcLys | Leu | Leu |

TABLE 2-continued

Peptide sequences of hits from the SIRT1 combinatorial library screen

| Sequence Identifiers | Position −2 | Position −1 | Position 0 | Position +1 | Position +2 |
|---|---|---|---|---|---|
| SEQ ID NO: 36-37 | Me₂Arg | Phe | AcLys | Pro | Glu |
| SEQ ID NO: 38 | Nle | Nle | AcLys | Gln | Gln |
| SEQ ID NO: 39 | Trp | Gly | AcLys | Ser | Pro |
| SEQ ID NO: 40-41 | Phe | Glu | AcLys | Tyr | Me₂Arg |
| SEQ ID NO: 42 | Trp | Pro | AcLys | Trp | Gln |
| SEQ ID NO: 43-44 | Me₂Arg | Ala | AcLys | Nle | Asp |
| SEQ ID NO: 45 | Gly | Thr | AcLys | Thr | Gly |
| SEQ ID NO: 46 | Gly | Tyr | AcLys | Pro | Thr |
| SEQ ID NO: 47 | Ile | Phe | AcLys | Thr | Phe |
| SEQ ID NO: 48 | Thr | Glu | AcLys | Gln | Glu |
| SEQ ID NO: 49 | His | Trp | AcLys | Thr | His |
| SEQ ID NO: 50 | Asp | Ser | AcLys | Gly | Ala |
| SEQ ID NO: 51 | Ser | Asp | AcLys | Tyr | His |
| SEQ ID NO: 52 | Asn | His | AcLys | Ile | Ile |
| SEQ ID NO: 53 | Trp | Trp | AcLys | His | Gly |
| SEQ ID NO: 54 | Pro | Ile | AcLys | Glu | Gln |
| SEQ ID NO: 55-56 | Me₂Arg | Pro | AcLys | Gln | Phe |
| SEQ ID NO: 57 | Asp | Val | AcLys | Nle | His |
| SEQ ID NO: 58 | Ile | Tyr | AcLys | Asn | Asp |
| SEQ ID NO: 59 | Thr | Pro | AcLys | Asn | Ala |
| SEQ ID NO: 60 | Pro | Gly | AcLys | Leu | Tyr |
| SEQ ID NO: 61-64 | Me₂Arg/Trp | Me₂Arg/Trp | AcLys | Ile | Thr |
| SEQ ID NO: 65-66 | Pro/Trp | Pro/Trp | AcLys | Ile | Thr |
| SEQ ID NO: 67-70 | Me₂Arg/Pro | Me₂Arg/Pro | AcLys | Ser | Ile |

Hit Sequencing with MALDI-MS

Beads from the enriched sample were pooled and washed with 8 M guanidinium hydrochloride (2×1 mL), doubly distilled water (10×1 mL) and DMF (3×1 mL). Individual beads were then deposited into separate microcentrifuge tubes containing 20 μL of cleavage cocktail (70% TFA, 30% doubly distilled water and 20% cyanogen bromide by weight), as described by Hu et al., 1999). After incubation overnight in the dark, the samples were dried and resuspended in 5 μL of 0.1% TFA. Each sample (1 μL) was combined with saturated matrix solution (1 μL) and dried on the target for MALDI-TOF MS analysis (positive ion mode).

Library Validation

To validate the results of the library screen, select hits and non-hits were resynthesized and subjected to in-solution kinetic analysis (Table 3). A radioactive TLC-based assay was employed with subsaturating levels of [$^{32}$P]-NAD⁺ to determine the relative catalytic efficiencies (Jackson et al., 2003, *J. Biol. Chem.* 278: 50985-50998). In addition, two "consensus" peptides containing residues occurring with the highest and lowest frequency at each position, independent of context, were analyzed. For comparison, a 5-mer comprised of a sequence corresponding to a known site for p53 deacetylation by SIRT1 was assayed (Table 3).

In Table 3, efficiencies ($^x$=average) were obtained by fitting the data from [$^{32}$P]-NAD⁺ assays to the modified Michaelis-Menten equation, $v=[k_{cat}/K_m)[S]]/(1+[S]/K_m)$. No definite catalytic efficiency for VQ(AcK)II SEQ ID NO: 31) was established due to problems with insolubility; a lower limit was established. Catalytic efficiencies of peptides containing the residues of the highest[b]/lowest[c] frequency at each position and the sequence relevant to p53 deacetylation in vivo[d] are shown for comparison.

TABLE 3

Peptide sequences and catalytic efficiencies of resynthesized select hits and non-hits from the SIRT1 peptide library screen

| | Peptide | $k_{cat}/K_m$ (x $10^{-3}$ $M^{-1}$ $S^{-1}$) |
|---|---|---|
| | Select Hits | |
| SEQ ID NO: 13 | QP(AcK)QI | 27.2 ± 4.2 |
| SEQ ID NO: 14 | Me$_2$RP(AcK)QF | 14.7 ± 3.2 |
| SEQ ID NO: 15 | Me$_2$RP(AcK)SI | 8.36 ± 0.57 |
| SEQ ID NO: 16 | NH(AcK)II | 3.63 ± 0.80 |
| SEQ ID NO: 17 | WH(AcK)FQ | 3.29 ± 0.43[x] |
| SEQ ID NO: 18 | VQ(AcK)II[a] | ≥2.47 ± 1.27[x] |
| | Select Non-hits | |
| SEQ ID NO: 19 | AY(AcK)EV | 5.32 ± 0.63 |
| SEQ ID NO: 20 | QNle(AcK)GF | 2.37 ± 0.14 |
| SEQ ID NO: 21 | LNle((AcK)VG | 1.61 ± 0.48[x] |
| | For Comparison | |
| SEQ ID NO: 22 | WH(AcK)QQ[b] | 7.23 ± 1.12 |
| SEQ ID NO: 23 | WP(AcK)QQ[b] | 1.54 ± 1.06 |
| SEQ ID NO: 24 | EL(AcK)AS[c] | 1.39 ± 0.10 |
| SEQ ID NO: 25 | HK(AcK)LM[d] | 3.11 ± 0.45 |

Hit sequences had significantly higher catalytic activity than non-hits. Some hits were near or greater than an order of magnitude more catalytically active than their non-hit counterparts. Hits correlated with increased catalytic activity by as much as 20-fold. Most hit sequences assayed in solution had significantly higher activity than the peptide sequence relevant to in vivo p53 deacetylation. One non-hit sequence AY(AcK)EV (SEQ ID NO: 19) had a catalytic activity comparable to those of a few of the hits.

Although the apparent second order rate constant ($k_{cat}/K_m$) varied widely among the peptides tested, the turnover number ($k_{cat}$) was relatively constant at ~0.1 $s^{-1}$. Differences in $k_{cat}/K_m$ reflect differences in peptide binding affinity.

One of the main advantages of this OBOC library is its context-specific nature. In other words, there is no implicit assumption that residues in substrate sequences function independently of one another. While oriented peptide libraries can be useful in resolving globally-preferred "consensus" sequences (Songyang et al., 1994; Blander et al., 2005) they do not provide contextual information.

The so-called "consensus" peptides WH(Ack)QQ (SEQ ID NO: 22) and WP(AcK)QQ (SEQ ID NO: 23) show a seven-fold difference in catalytic activity in favor of WH(AcK)QQ (SEQ ID NO: 22) (Table 3). Thus, in the context of WX(AcK)QQ (SEQ ID NO: 72), a histidine is greatly preferred at position −1. Within the XP(AcK)QX context (SEQ ID NO: 73), QP(AcK)QI (SEQ ID NO: 30) is favored over WP(AcK)QQ (SEQ ID NO: 23) by 18-fold. Thus, SIRT1 mediated deacetylation is stringently context dependent and that there is no best "average sequence". Further support comes from the fact that although proline residues (at −1) are not well tolerated when adjacent to a tryptophan at −2, they appear to function well when adjacent to dimethyl arginine at −2. There are synergistic/anagonistic relationships among certain residues and that this plays a significant role in substrate recognition by SIRT1.

BLAST searches of the SIRT1 hits (Table 2) within the mammalian proteome reveal correspondence to a number of proteins (Table 4), some of which are known to be acetylated in vivo.

TABLE 4

BLAST searches of SIRT1 hit sequences

| Sequence ID | Hit Sequence | Protein (name, accession, relevant sequence) |
|---|---|---|
| SEQ ID NO: 26 | LNKDQ | Moesin, NP_002435, [Homo sapiens] |
| | | MSN protein, AAH11827[Homo sapiens] |
| SEQ ID NO: 27 | WHKFQ | chondroitin sulfate proteoglycan, 2 NP_004376, [Homo sapiens] |
| SEQ ID NO: 28 | WHKFE | dual oxidase 1 precursor, NP_059130 [Homo sapiens] |
| | | NADPH thyroid oxidase 2, AAF73922, [Homo sapiens] |
| SEQ ID NO: 29 | SYKQW | fatty acid coenzyme A ligase 5, BAA86054 [Homo sapiens] |

TABLE 4-continued

BLAST searches of SIRT1 hit sequences

| Sequence ID | Hit Sequence | Protein (name, accession, relevant sequence) |
|---|---|---|
| SEQ ID NO: 30 | QPKQI | Notch homolog 4 (*Drosophila*), CAI17543 [*Homo sapiens*]<br>Orphan sodium- and chloride-dependent neurotransmitter transporter, Q9GZN6, [*Homo sapiens*]<br>SLC6A16 protein, AAH34948 [*Homo sapiens*]<br>TPA: class II bHLH protein scleraxis, DAA00239 [*Homo sapiens*]<br>U5 snRNP-specific protein, AAH64370 [*Homo sapiens*]<br>apoptosis-regulated protein 1, AAS64748 [*Homo sapiens*] |
| SEQ ID NO: 31 | VQKII | Werner syndrome, AAR05448 [*Homo sapiens*]<br>chaperonin containing TCP1, subunit 6B, NP_006575 [*Homo sapiens*]<br>MGC16733 protein, AAH09995 [*Homo sapiens*]<br>chemokine (C-X-C motif) ligand 3, NP_002081 [*Homo sapiens*]<br>MDN1 protein, AAH14882 [*Homo sapiens*]<br>LOC150159 protein, AAH46636 [*Homo sapiens*]<br>C9orf72 protein, AAH68445 [*Homo sapiens*] |
| SEQ ID NO: 32 | HRKMP | SCAM-1 protein, AAH67260 [*Homo sapiens*]<br>SH3-containing adaptor molecule-1, AAC09244 [*Homo sapiens*]<br>KIAA1792 protein, BAB47421 [*Homo sapiens*]<br>RP5-1187M17.5, CAC32460 [*Homo sapiens*]<br>MSTP060, AAO15306 [*Homo sapiens*]<br>LAS1-like, NP_112483 [*Homo sapiens*]<br>OTTHUMP00000021323, CAH70992 [*Homo sapiens*] |
| SEQ ID NO: 33 | HKKMP | FLJ00158 protein, BA884913 [*Homo sapiens*] |
| SEQ ID NO: 34 | AVKFM | secreted frizzled-related protein 5, CA114274 [*Homo sapiens*]<br>RAN binding protein 17 [*Homo sapiens*] |
| SEQ ID NO: 35 | NHKLL | protocadherin 11, AAK13468 [*Homo sapiens*]<br>engulfment and cell motility 3, NP_078988 [*Homo sapiens*]<br>PARP8 protein, AAH37386 [*Homo sapiens*]<br>complement component 3, AAR89906 [*Homo sapiens*]<br>WD repeat domain 35, isoform 2, AAH36659 [*Homo sapiens*] |
| SEQ ID NO: 36 | RFKPE | solute carrier family 30 (zinc transporter), NP_037441 member 4 [*Homo sapiens*]<br>ubiquitin specific protease 53, NP_061923 XP_052597 [*Homo sapiens*]<br>membrane-associated guanylate kinase-related 3 (MAGI-3), CAH70944 [*Homo sapiens*]<br>zinc transporter 4, AAB82561 [*Homo sapiens*]<br>KIAA1350 protein, BAA92588 [*Homo sapiens*]<br>cytochrome P450, family 2, subfamily E, polypeptide 1, NP_000764 [*Homo sapiens*] |
| SEQ ID NO: 37 | KFKPE | Pleckstrin homology domain containing, family A (phosphoinositide binding specific) member 3, AAH44567 [*Homo sapiens*]<br>Phosphoinositol 4-phosphate Adaptor Protein-1, AAG15199 [*Homo sapiens*] |
| SEQ ID NO: 38 | MMKQQ | golgi antigen gcp372, BAA05025 [*Homo sapiens*]<br>giantin, CAA53052 [*Homo sapiens*] |
| SEQ ID NO: 39 | WGKSP | apolipoprotein L5, NP_085145 [*Homo sapiens*]<br>NY-REN-55 antigen, AAD42879 [*Homo sapiens*]<br>NIMA (never in mitosis gene a)-related kinase 1, NP_036356 XP_291107 [*Homo sapiens*]<br>KIAA1901 protein, BAB67794 [*Homo sapiens*]<br>UDP-N-acetylglucosamine: alpha-1,3-D-mannoside beta-1,4-N-acetylglucosaminyltransferase IV, NP_080519 [*Mus musculus*] |
| SEQ ID NO: 40 | FEKYR | protocadherin gamma A11, AAD43765 [*Homo sapiens*]<br>signal-induced proliferation-associated 1 like 1, NP_056371 [*Homo sapiens*]<br>high-risk human papilloma viruses E6 oncoproteins targeted protein E6TP1 alpha; putative GAP protein alpha, AAD12543 [*Homo sapiens*]<br>KIAA0440, BAA23712 [*Homo sapiens*]<br>spa-1-like; similar to AF026504 (PID:g2555183), AAC83179 [*Homo sapiens*]<br>PRO0097, AAF24015 [*Homo sapiens*] |

TABLE 4-continued

BLAST searches of SIRT1 hit sequences

| Sequence ID | Hit Sequence | Protein (name, accession, relevant sequence) |
|---|---|---|
| SEQ ID NO: 41 | FEKYK | Nebulin, P20929 [Homo sapiens] |
| SEQ ID NO: 42 | WPKWQ | No identical sequence match |
| SEQ ID NO: 43 | RAKMD | large tumor suppressor 1, AAD16882 [Homo sapiens]<br>LATS, large tumor suppressor, homolog 2, NP_055387 [Homo sapiens]<br>amyloid precursor-like protein 1, AAB50173 [Homo sapiens]<br>potassium channel, subfamily T, member 1, NP_065873 XP_029962 [Homo sapiens]<br>LOH12CR1, AAK71328 [Homo sapiens]<br>olfactomedin 1, AAP35810 [Homo sapiens]<br>Zinc finger protein 541, AA101053 [Homo sapiens]<br>p33, AAG11396 [Homo sapiens]<br>nucleobindin 1, AAP88830 [Homo sapiens] |
| SEQ ID NO: 44 | KAKMD | mel transforming oncogene, NP_005361 [Homo sapiens]<br>T cell receptor beta variable 21/OR9-2, CAH69869 [Homo sapiens] |
| SEQ ID NO: 45 | GTKTG | WD repeat domain 3, CAI22739 [Homo sapiens]<br>cytoplasmic linker 2 isoform 1, NP_003379 [Homo sapiens]<br>KIAA1858 protein, BAB47487 [Homo sapiens]<br>exophilin 5, AAM44402 [Homo sapiens] |
| SEQ ID NO: 46 | GYKPT | complement component 4 binding protein, alpha, CAH70782 [Homo sapiens]<br>KCRM_HUMAN; M-CK, AAC62841 [Homo sapiens]<br>creatine kinase, muscle, AAP35439 [Homo sapiens] |
| SEQ ID NO: 47 | IFKTF | cullin 4B, AAR13073 [Homo sapiens]<br>KIAA0695 protein, BAA31670 [Homo sapiens] |
| SEQ ID NO: 48 | TEKQE | caspase recruitment domain family, member 11, EAL23962 [Homo sapiens]<br>CARD-containing MAGUK protein CARMA1, AAL34460 [Homo sapiens]<br>oligophrenin-1 like protein, AAd39482 [Homo sapiens]<br>GTPase regulator associated with the focal adhesion kinase pp125, NP_055886 [Homo sapiens]<br>myosin phosphatase-Rho interacting protein, AAQ63176 [Homo sapiens]<br>HLC-8, AAO25513 [Homo sapiens]<br>cardiomyopathy associated protein 1, AAQ64003 [Homo sapiens]<br>TRAF family member-associated Nf-kappa B activator, NP_665731 [Rattus norvegicus]<br>RCSD1 protein, AAH98426 [Homo sapiens] |
| SEQ ID NO: 49 | HWKTH | No identical sequence match |
| SEQ ID NO: 50 | DSKGA | dentin sialophosphoprotein preproprotein, NP_055023 [Homo sapiens]<br>Monoglyceride lipase, AAH00551 [Homo sapiens]<br>EGF domain-containing protein, AAP35084 [Homo sapiens]<br>Protein phosphatase 1, regulatory (inhibitor) subunit 1A, AAH22470 [Homo sapiens]<br>RNA binding motif protein 19, NP_057280 [Homo sapiens]<br>MEGF8, BAA32469 [Homo sapiens]<br>zinc finger protein 608, NP_065798 XP_114432 [Homo sapiens]<br>valyl-tRNA-synthetase G7a/Bat6, AAL14460 [Mus musculus] |
| SEQ ID NO: 51 | SDKYH | Deoxycytidylate deaminase, P32321 (dCMP deaminase) |
| SEQ ID NO: 52 | NHKII | zinc finger protein 588, NP_057304 [Homo sapiens]<br>zinc finger protein 15-like 1 (KOX 8), NP_067092 [Homo sapiens]<br>UDP-Gal:betaGlcNAc beta 1,4-galactosyltransferase 6 variant, BAD92431 [Homo sapiens]<br>SMAP-7, BAB20272 [Homo sapiens] |
| SEQ ID NO: 53 | WWKHG | No identical sequence matches |
| SEQ ID NO: 54 | PIKEQ | procollagen, type XII, alpha 1, NP_031756 [Mus musculus] |

TABLE 4-continued

BLAST searches of SIRT1 hit sequences

| Sequence ID | Hit Sequence | Protein (name, accession, relevant sequence) |
|---|---|---|
| SEQ ID NO: 55 | RPKQF | RNA guanylyltransferase, AA888903 [*Mus musculus*]<br>KIAA0992 protein, BAA76836 [*Homo sapiens*]<br>N-methylpurine-DNA glycosylase isoform, aNP_002425 [*Homo sapiens*] |
| SEQ ID NO: 56 | KPKQF | RP11-334P12.2, CAH71251 [*Homo sapiens*]<br>cell adhesion kinase beta, AAC05330 [*Homo sapiens*]<br>RNA binding motif protein 7, AAH34381 [*Homo sapiens*]<br>PTK2B protein tyrosine kinase 2 beta isoform a, NP_775266 [*Homo sapiens*]<br>Neuronal amiloride-sensitive cation channel 1, isoform 2, AAH75043 [*Homo sapiens*]<br>RNA helicase, AAD19826 [*Homo sapiens*]<br>focal adhesion kinase, AAB47217 [*Homo sapiens*] |
| SEQ ID NO: 57 | DVKMH | No identical sequence matches |
| SEQ ID NO: 58 | IYKND | immunoglobulin superfamily receptor translocation associated 2(IRTA2), CAH71429 [*Homo sapiens*]<br>ROS1, AAA60277 [*Homo sapiens*]<br>G protein-coupled receptor 119, AAP72132 [*Mus musculus*]<br>transmembrane protein kinase 3), AAA36580 [*Homo sapiens*]<br>Fc receptor-like protein 5, AAK93971 [*Homo sapiens*]<br>v-ros UR2 sarcoma virus oncogene homolog 1 (avian), CAI42375 [*Homo sapiens*] |
| SEQ ID NO: 59 | TPKNA | zinc finger protein 440 like, NP_001012771 XP_371138 [*Homo sapiens*]<br>adenosine deaminase, RNA-specific, 82, NP_443209 [*Mus musculus*] |
| SEQ ID NO: 60 | PGKLY | Phosphatidylethanolamine binding protein, AAH08169 [*Mus musculus*] |
| SEQ ID NO: 61 | RWKIT | integrin beta 4, NP_037312 [*Rattus norvegicus*] |
| SEQ ID NO: 62 | KWKIT | desmoglein 2, NP_031909 [*Mus musculus*] |
| SEQ ID NO: 63 | WRKIT | chromosome 6 open reading frame 103, CAI16490 [*Homo sapiens*] |
| SEQ ID NO: 64 | WKKIT | No identical sequence match |
| SEQ ID NO: 65 | WPKIT | EPB41L5 protein, AAH32822 [*Homo sapiens*]<br>erythrocyte membrane protein band 4.1 like 4B isoform 1, NP_060894 [*Homo sapiens*]<br>EHM2, BAA96079 [*Homo sapiens*]<br>KIAA1548 protein, BAB13374 [*Homo sapiens*]<br>beta-crystallin, AAA52107 [*Homo sapiens*] |
| SEQ ID NO: 66 | PWKIT | REPS1 protein, AAH21211 [*Homo sapiens*]<br>RALBP1 associated Eps domain containing 1, CAI42879 [*Homo sapiens*]<br>sodium potassium chloride cotransporter 2, NP_000329 [*Homo sapiens*] |
| SEQ ID NO: 67 | RPKSI | alpha(1,3)-fucosyltransferase; ELFT, AAB20349 [*Homo sapiens*]<br>nuclear factor I, AAB52369 [*Homo sapiens*]<br>fucosyltransferase 4, NP_002024 [*Homo sapiens*]<br>ELAM-1 ligand fucosyltransferase, AAA63172 [*Homo sapiens*]<br>calmodulin regulated spectrin-associated protein 1-like 1, NP_982284 XP_036589 [*Homo sapiens*]<br>CAMSAP1L1 protein, AAH11385 [*Homo sapiens*] |
| SEQ ID NO: 68 | KPKSI | Transient receptor potential cation channel subfamily M member 7 (Long transient receptor potential channel 7) (LTrpC7) (Channel-kinase 1), Q96QT4 [*Homo sapiens*]<br>Synapse-associated protein 102, AAH93864 [*Homo sapiens*]<br>C21orf7 form C, AAF81753 [*Homo sapiens*]<br>c21orf7 form B, AAF81752 [*Homo sapiens*]<br>TAK1-like protein, AAO16519 [*Homo sapiens*]<br>MAP4K3, AAN75849 [*Homo sapiens*]<br>channel-kinase 1, AAK19738 [*Homo sapiens*]<br>transcription factor GATA-6, NP_999493 [*Sus scrota*] |

TABLE 4-continued

BLAST searches of SIRT1 hit sequences

| Sequence ID | Hit Sequence | Protein (name, accession, relevant sequence) |
|---|---|---|
| SEQ ID NO: 69 | PRKSI | poly (ADP-ribose) polymerase family, member 6 isoform 1, NP_064598 [Homo sapiens]<br>C19orf2 protein, AAH14933 [Homo sapiens]<br>RPB5-mediating protein, isoform b, AAH67259 [Homo sapiens]<br>NNX3, AAD08679 [Homo sapiens] |
| SEQ ID NO: 70 | PKKSI | zinc finger protein 318, CAH71374 [Homo sapiens]<br>Alanyl-tRNA synthetase, AAH11451 [Homo sapiens]<br>histone H1, AAN06703 [Homo sapiens]<br>nucleoporin, BAB18537 [Homo sapiens]<br>Inner membrane protein, mitochondrial, AAH02412 [Homo sapiens]<br>ZNF318 protein, AAH30687 [Homo sapiens] |

Example 2. Use of a Combinatorial Library to Identify Histone-Specific Protein Binding General An OBOC histone H4N-terminal tail combinatorial library was constructed to identify the binding preferences of the antibody toward all known possible histone modification states. The H4 histone tail library was comprised of the sequence corresponding to the first 21 amino acids of human histone H4 attached to a linker composed of 2 β-alanines (B) and a methionine (M). The library included 800 unique peptide sequences, representing all known modification states for the first 21 amino acids of histone H4 in addition to all possible methylation states at lysines and arginines that are known to be methylated. Using an α-phos (S1) H4 antibody as a primary antibody, the library was screened to determine histone H4N-terminal sequences to which the primary antibody specifically bound.

Amino acid derivatives and resins were purchased from Peptides International (Louisville, Ky.), Novabiochem (San Diego, Calif.), or from Bachem (Bubendorf, Switzerland). Other chemical reagents were obtained from Sigma-Aldrich, Invitrogen (Carlsbad, Calif.), or Jackson ImmunoResearch Laboratories (West Grove, Pa.). The α-phos (S1) H4 antibody was a gift from the laboratory of C. David Allis (Rockefeller University, New York, N.Y.). Peptides were synthesized on a Symphony synthesizer from Protein Technologies (Tucson, Ariz.). Filter columns for on-bead assays were obtained from Alltech (Deerfield, Ill.).

Analytical gradient HPLC was performed on a Shimadzu series 2010C HPLC with a Vydac C18 column (10 μm, 4.6×250 mm). All runs employed linear gradients of 0.05% aqueous TFA and 0.02% TFA in acetonitrile. Microextraction tips for desalting peptides were purchased from Varian, Inc. (Palo Alto, Calif.). MALDI-TOF MS was performed on a Bruker REFLEX II and MALDI TOF-TOF MS was executed on an Applied Biosystems 4800. A Zeiss Axioplan 2 microscope (Jena, Germany) with a DAPI dye bandpass filter (390-410 nm) and an AxioCam MRm was used for fluorescence microscopy.

On-Bead Assay with Peptide Standards

Five-mg quantities of TentaGel Macrobead $NH_2$ resin (280-320 μm, 0.27 mmol/g loading, 65,550 beads/g) bearing either a phosphorylated or unphosphorylated histone H4 sequence (or a mixture) were added to 1.5 mL filter columns, washed thoroughly with DCM, MeOH, doubly distilled water (dd$H_2$O) and PBST buffer (25 mM NaPi, pH 7.4, 150 mM NaCl, and 0.1% Tween 20). The resin was swelled for 1 hour with gentle rocking prior to drainage and one hour of blocking with 3% (w/v) bovine serum albumin (BSA) in PBST. After draining the blocking solution to the resin bed, 100 μL of a 100:1 dilution of α-phos (S1) H4 antibody in PBST containing 3% BSA was added and the resin was allowed to rock gently for one hour.

After draining to the resin bed, the resin was washed 3×100 μL PBST and 100 μL of 50 nM biotinylated goat-anti-rabbit antibody in PBST containing 3% BSA was added. One hour of gentle rocking was followed by draining the solution to the resin bed and washing 3×100 μL PBST.

The resin was incubated with 100 μL of 25 nM solution of Q-dot 605 streptavidin conjugate in PBST and gently rocked for 2 hours. Following drainage to the resin bed, the resin was washed 10×200 μL PBST. The resin was then resuspended in PBST and viewed under a fluorescence microscope.

Library Construction

The combinatorial histone H4 peptide library was constructed on TentaGel Macrobead $NH_2$ resin (280-320 μm, 0.27 mmol/g loading, 65,550 beads/g) using the split-pool approach (Lam et al., 1991, Nature 354: 82-84; Furka et al., 1991, Int. J. Pept. Protein Res. 37: 487-493) for sites of variability. Sites of variability include positions 20 (K, AcK, MeK, $Me_2K$, $Me_3K$), 16 (K,AcK), 12 (K,AcK), 8 (K,AcK), 5 (K,AcK), 3 (R, MeR, $Me_2R_{symmetric}$, $Me_2R_{asymmetric}$, citrulline) and 1 (S, pS). The synthesis was performed on a 50 μmol scale with standard Fmoc/tBu chemistry (Bodanszky M., 1993, Principles of Peptide Synthesis, 2nd ed., Springer-Verlag, Germany). All amino acids (at least 4.7 equivalents/coupling) were double coupled for 2 hour time periods.

Prior to the partially randomized histone H4 sequence, a 3 amino acid linker, BBM (where B=β-alanine, M=methionine) was synthesized. After the final N-terminal deprotection, the N-termini of all the peptides were acetylated with acetic anhdyride. A 50 mg (13.5 μmol) portion of the library was deprotected for 5 hours with Reagent K (TFA/EDT/thioanisole/water/phenol: 82.5%, 2.5%, 5%, 5%, 5%) prior to use, as described by King et al., 1990, Int. J. Pept. Protein Res. 36: 255-266. The remainder of the library was stored at 4° C. for later use.

Evaluation of Integrity of the Peptide Library

Twenty beads were randomly selected from the library and deposited into separate microcentrifuge tubes containing 20 μL of cleavage cocktail (70% TFA, 30% dd$H_2$O and 20% cyanogen bromide by weight; Hu et al., 1999, Biochemistry 38: 643-650). After incubation overnight in the dark, the samples were dried.

Ten of the cleavage products were desalted and sequenced by MALDI TOF-TOF MS. The remaining 10 cleavage products were dissolved in 1004 quantities of ddH$_2$O and analyzed by analytical RP-HPLC. Fractions corresponding to the primary peak at 214 nm were lyophilized and resuspended in 5 µL of ddH$_2$O. Each sample (1 µL) was combined with saturated matrix solution (1 µL) and dried on the target for MALDI-TOF MS analysis (positive ion mode).

On-Bead Library Prescreen and Screen

Prescreen was performed by adding 50 mg (13.5 µmol) of the peptide library to a 4 mL filter column and washing it thoroughly with DCM, MeOH, ddH$_2$O and PBST buffer. The resin was swelled for 1 hour with gentle rocking prior to drainage and one hour of blocking with 3% BSA in PBST. After draining the blocking solution to the resin bed, 1 mL of 50 nM biotinylated goat-anti-rabbit antibody in PBST containing 3% BSA was added. Following 1 hour of rocking, the solution was drained to the resin bed and washed 3×1 mL PBST. The resin was then rocked with 1 mL of a 25 nM solution of Q-dot 605 streptavidin conjugate in PBST for two hours. Following drainage to the resin bed, the resin was washed 10×2 mL PBST. At this point, the resin was resuspended in PBST and viewed under a fluorescent microscope and any fluorescent beads could be removed from the library.

After prescreening the library for nonspecific interactions with the secondary antibody or the quantum dots, a screen was performed. The only difference from the prescreen was a one hour incubation with 1 mL of a 100:1 dilution of α-phos (S1) H4 in PBST with 3% BSA after the swell step and washing 3×1 mL PBST prior to addition of the secondary antibody. When viewed under the microscope, a number of brightly fluorescent, moderately fluorescent and dark beads were manually selected.

Peptide Sequencing with MALDI TOF-TOF MS

Beads that were selected under the microscope were incubated with 200 µL of 8 M guanidinium hydrochloride prior to washing 3×500 µL ddH$_2$O and drying. Peptides were cyanogen bromide cleaved from each bead and desalted before sequencing with MALDI TOF-TOF MS.

On-Bead Western Analysis

Figure 8:
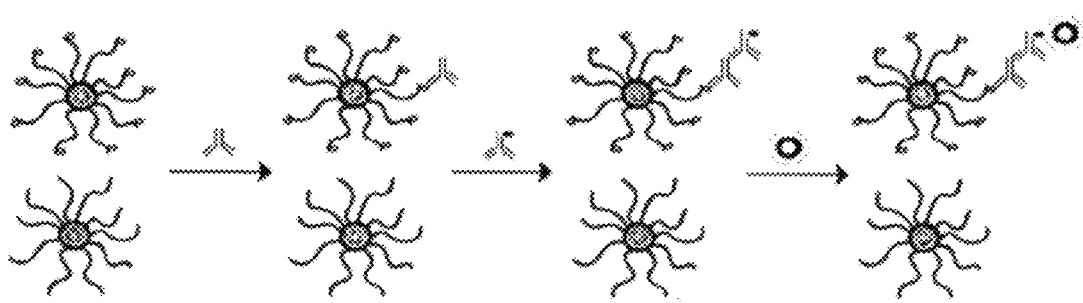
FIG. 8 schematically depicts the on-bead Western analysis. Beads with phosphorylated sequences (top) or unphosphorylated sequences (bottom) corresponding to the N-terminal tails of histone H4 were assayed.

FIG. 8 shows schematically the on-bead Western (immunoprecipitation) analysis with control peptides. FIG. 8 shows the on-bead assay, beads with phosphorylated sequences (top; phosphorylation depicted as gray ovals attached to peptide chains) or unphosphorylated sequences (bottom; naked peptide chains) corresponding to the N-terminal tails of histone H4 are first incubated with α-phos (S1) H4 antibody. After a washing step, a biotinylated secondary antibody directed towards the primary antibody is added. After another washing step, streptavidin-coated quantum dots are incubated with the beads.

Figure 9:
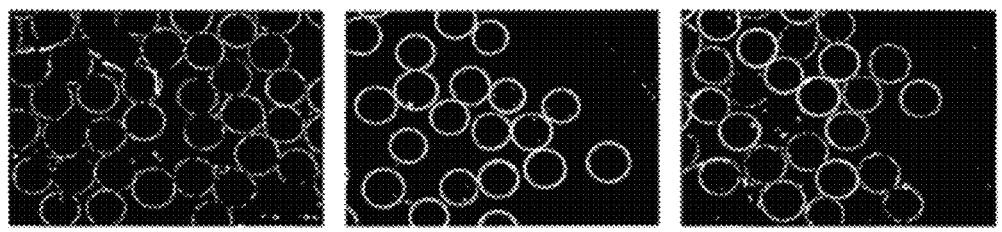
FIG. 9 shows images of fluorescence micrographs of the on-bead Western analysis. Left panel, fluorescent microscopic image of AcSGRGKGG(AcK)GLG(AcK)GGAKRHRKVBBM-Macrobead (1) (SEQ ID NO:1) after the on-bead assay. Center panel, fluorescent microscopic image of AcpSGRGKGG(AcK)GLG(AcK)GGAKRHRK-VBBM-Macrobead (2) (SEQ ID NO:2). Right panel, fluorescent microscopic image of a 5:1 ratio of (1) to (2). B refers to beta-alanine.

FIG. 9 shows: (left panel) fluorescent microscopic image of AcSGRGKGG(AcK)GLG(AcK)GGAKRHRKVBBM-Macrobead (1) (SEQ ID NO:1) after the on-bead assay; (center panel) a fluorescent microscopic image of AcpS-GRGKGG(AcK)GLG(AcK)GGAKRHRKVBBM-Macrobead (2) (SEQ ID NO:2); (right panel) a fluorescent microscopic image of a 5:1 ratio of (1) to (2). B=beta-alanine.

Figure 10:
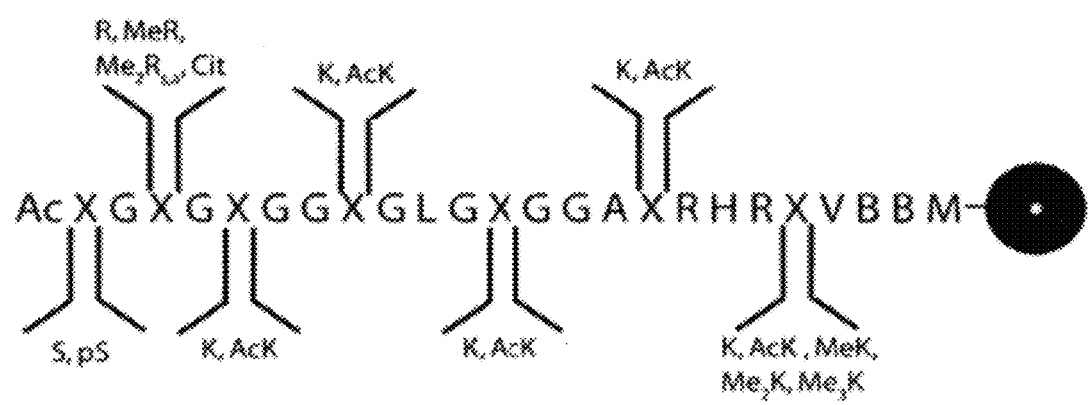
FIG. 10 illustrates the H4 histone N-terminal tail library, which is comprised of the sequence (SEQ ID NO:71)

After demonstrating detection of serine phosphorylation of a histone H4 sequence immobilized on a bead (FIG. 9), an OBOC histone H4 combinatorial library (H4 histone N-terminal tail library) was constructed to further examine the binding preferences of the antibody toward all known possible histone modification states. The H4 histone tail library, schematically shown in FIG. 10, is comprised of the sequence corresponding to the first 21 amino acids of human histone H4 attached to a linker composed of 2 β-alanines (B) and a methionine (M). Sites for modification include positions 20, 16, 12, 8, 5, 3 and 1 and are annotated with X. Possible modification states are shown above or below the peptide chain (FIG. 10). In this library, schematically shown in FIG. 10, the first 21 amino acids of histone H4 are represented with 7 sites of variability. The sites include positions 20 (K, AcK, MeK, Me$_2$K, Me$_3$K), 16 (K,AcK), 12 (K,AcK), 8 (K,AcK), 5 (K,AcK), 3 (R, MeR, Me$_2$R$_{symmetric}$, Me$_2$R$_{asymmetric}$, citrulline) and 1 (S, pS). This library includes all known modification states for the first 21 amino acids of histone H4 in addition to all possible methylation states at lysines and arginines that are known to be methylated. Therefore, this library is composed of 800 unique peptide sequences with 99% confidence of 95% coverage of combinatorial space (each library consists of ~50 mg of resin; Burgess et al., *J. Med. Chem.* 37: 2985-2987).

The library synthesis was followed by rigorous evaluation of the synthetic product. RP-HPLC analysis of the cleavage products from 10 individual beads revealed peptides of ~90-95% purity within the correct mass range. In addition, the cleavage products from 10 additional randomly selected beads were successfully sequenced with MALDI TOF-TOF MS.

The library was first prescreened with only the secondary antibody and quantum dots. The fact that none of the beads exhibited fluorescence due to quantum dots suggested the absence of non-specific interactions between the immobilized peptides with either the secondary antibody or the quantum dots. Therefore, when the primary antibody was included in a screening experiment, the fluorescence observed was due to a specific interaction with the primary antibody (FIG. 11). Of the library, about half of the beads exhibited some level of quantum dot-associated fluorescence. A number of individual beads of were manually selected and classified as either: fluorescent, moderately fluorescent or dark.

FIG. 11 shows a fluorescent microscopic image of the results of a H4 library screen with α-phos (S1) H4 antibody, which was used as a primary antibody. The fluorescence intensity is indicative of the degree of interaction of peptides with the α-phos (S1) H4 antibody. A number of beads were manually selected for peptide sequencing based on their fluorescence intensity.

Data from the screen indicate the binding preferences of the α-phos (S1) H4 antibody for certain sequences (Table 5). Twenty beads were manually selected from a screen of a histone H4 tail library. Sequences were elucidated by MALDI TOF-TOF MS. All sequences obtained from fluorescent beads were phosphorylated while the moderately fluorescent beads displayed peptides that were typically phosphorylated (and generally highly-modified). Eighty percent of the dark beads harbored peptides that were unphosphorylated. Legend: pS=phosphorylated serine, AcK=acetylated lysine, MeK, Me$_2$K, Me$_3$K=the correspondingly methylated states of lysine, MeR and Me$_2$R=the correspondingly methylated states of arginine where (a) and (s) refer to symmetric and asymmetric respectively.

TABLE 5

Binding preferences of the α-phos (S1) H4 antibody

| Bead Fluorescence | Position 1 | Position 3 | Position 5 | Position 8 | Position 12 | Position 16 | Position 20 |
|---|---|---|---|---|---|---|---|
| Fluorescent | pS | Mc$_2$R (a) | AcK | K | K | AcK | MeK |
| Fluorescent | pS | Me$_2$R (a) | K/AcK | K/AcK | K | K | MeK |
| Fluorescent | pS | Me$_2$R (a) | K | AcK | MeK | K | AcK |
| Fluorescent | pS | MeR | AcK | AcK | K | K | AcK/Me$_3$K |
| Fluorescent | pS | R | K | AcK | Me$_2$K | K | MeK |
| Fluorescent | pS | MeR | K | AcK | K | K | AcK/Me$_3$K |
| Fluorescent | pS | R | K | K | AcK/Me$_3$K | K | MeK |
| Fluorescent | | | | Poor quality (3 beads) | | | |
| Moderately Fluorescent | pS | MeR | AcK | AcK | Ack/Me$_3$K | AcK | Me$_2$K |
| Moderately Fluorescent | pS | Me$_2$R (s) | AcK | AcK | MeK | AcK | Me$_2$K |
| Moderately Fluorescent | S | Me$_2$R (s) | AcK | AcK | Me2K | K | K |
| Moderately Fluorescent | | | Poor quality (but appear to be phosphorylated and heavily modified - 2 beads) | | | | |
| Dark | S | Me$_2$R (s) | K | K | MeK | K | K |
| Dark | S | R | K | K | Me$_2$K | K | AcK/Me$_3$K |
| Dark | pS | Me$_2$R (s) | K | AcK | AcK/Me$_3$K | AcK | MeK |
| Dark | S | MeR | K | K | AcK | K | MeK |
| Dark | S | MeR | K | K | Me$_2$K | K | Me$_3$K |

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in clinical prevention and therapy, obvious to those skilled in the art, are within the scope of this invention. All publications, patents, and patent applications cited herein are incorporated by reference in their entirety for all purposes.

What is claimed is:

1. A combinatorial library comprising a collection of peptides, wherein each peptide in the collection of peptides comprises at least 5 consecutive amino acid residues having an amino acid sequence located in the first 21 N-terminal residues of the structure of the polypeptide in FIG. 10 (SEQ ID NO: 71), wherein B is β-alanine, X is indicative of the amino acid or modified amino acid as shown above or below X in the peptide amino acid sequence, wherein Me is methylation, Ac is acetylation, p is phosphorylation, Cit is citrulline, subscript s is symmetric and subscript a is asymmetric, wherein each peptide in the collection of peptides is differentially covalently modified and wherein each peptide in the collection of peptides has at least two different covalent modifications to at least two different amino acid residues of each peptide in the collection of peptides, wherein the covalent modifications are selected from acetylation of lysine, methylation of lysine or arginine, citrullination, of arginine, phosphorylation of serine, threonine or tyrosine, ubiquitination of lysine, sumoylation of lysine and ADP ribosylation of arginine, aspartic acid or glutamic acid, and wherein each peptide in the collection of peptides is covalently attached to a linker thereby forming a peptide-linker complex, wherein each of the peptide-linker complexes is attached to a plurality of non-natural solid phase supports such that each solid phase support has a peptide with the same covalent modifications to the same amino acid residues attached thereto.

2. The combinatorial library of claim 1, wherein at least one of the covalent modifications comprises citrullination of an arginine in at least one peptide of the collection of peptides.

3. The combinatorial library of claim 1, wherein at least one of the covalent modifications comprises acetylation of a lysine in at least one peptide of the collection of peptides.

4. The combinatorial library of claim 1, wherein at least one of the covalent modifications comprises methylation of a lysine or arginine in at least one peptide of the collection of peptides.

5. The combinatorial library of claim 1, wherein at least one of the covalent modifications comprises phosphorylation of a serine, threonine or tyrosine in at least one peptide of the collection of peptides.

6. The combinatorial library of claim 1, wherein at least one of the covalent modifications comprises methylation of a lysine or arginine in at least one peptide of the collection of peptides, citrullination of an arginine in at least one peptide of the collection of peptides and acetylation of a lysine in at least one peptide of the collection of peptides.

7. The combinatorial library of claim 1, wherein at least one of the covalent modifications comprises ubiquitination of a lysine in at least one peptide of the collection of peptides.

8. The combinatorial library of claim 1, wherein at least one of the covalent modifications comprises sumoylation of a lysine in at least one peptide of the collection of peptides.

9. The combinatorial library of claim 1, wherein at least one of the covalent modifications comprises ADP-ribosylation of an arginine, aspartic acid or glutamic acid in at least one peptide of the collection of peptides.

10. The combinatorial library of claim 1, wherein the solid phase support is selected from beads, microarray, microplate or a chip.

11. A method of determining the binding specificity of a protein for a differentially covalently modified peptide comprising:

a) contacting the combinatorial library of claim 1 with a protein to allow binding of the protein to the combinatorial library, wherein the protein is capable of binding to at least one of the covalently modified peptides;

b) detecting the protein bound to the covalently modified peptides using a label; and c) determining the binding specificity of the protein for the covalently modified peptides.

* * * * *

UNITED STATES PATENT AND TRADEMARK OFFICE
CERTIFICATE OF CORRECTION

PATENT NO. : 9,988,665 B2
APPLICATION NO. : 13/208894
DATED : June 5, 2018
INVENTOR(S) : John M. Denu and Adam L. Garske It is certified that error appears in the above-identified patent and that said Letters Patent is hereby corrected as shown below:

Statement of Government Support Clause should read:
This invention was made with government support under GM065386 and GM059785 awarded by the National Institutes of Health. The government has certain rights in the invention.

Signed and Sealed this
Twenty-first Day of August, 2018

Andrei Iancu
*Director of the United States Patent and Trademark Office*

SEQUENCE LISTING

```
<160> NUMBER OF SEQ ID NOS: 74

<210> SEQ ID NO 1
<211> LENGTH: 24
<212> TYPE: PRT
<213> ORGANISM: Artificial Sequence
<220> FEATURE:
<223> OTHER INFORMATION: Macrobead
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (22)..(22)
<223> OTHER INFORMATION: bAla
<220> FEATURE:
<221> NAME/KEY: MOD_RES
<222> LOCATION: (23)..(23)
<223> OTHER INFORMATION: bAla

<400> SEQUENCE: 1

Ser Gly Arg Gly Lys Gly Gly Lys Gly Leu Gly Lys Gly Gly Ala Lys
1               5                   10                  15

Arg His Arg Lys Val Ala Ala Met
            20
```

```
<210> SEQ ID NO 2
<211> LENGTH: 24
<212> TYPE: PRT
<213> ORGANISM: Artificial Sequence
<220> FEATURE:
<223> OTHER INFORMATION: Macrobead
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (22)..(22)
<223> OTHER INFORMATION: bAla
<220> FEATURE:
<221> NAME/KEY: MOD_RES
<222> LOCATION: (23)..(23)
<223> OTHER INFORMATION: bAla

<400> SEQUENCE: 2

Ser Gly Arg Gly Lys Gly Gly Lys Gly Leu Gly Lys Gly Gly Ala Lys
1               5                   10                  15

Arg His Arg Lys Val Ala Ala Met
            20

<210> SEQ ID NO 3
<211> LENGTH: 5
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: ACETYLATION

<400> SEQUENCE: 3

Gly Gly Lys Ala Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: ACETYLATION
```

```
<400> SEQUENCE: 4

Thr Gly Gly Lys Ala Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: ACETYLATION

<400> SEQUENCE: 5

Ser Thr Gly Gly Lys Ala Pro
1               5

<210> SEQ ID NO 6
<211> LENGTH: 6
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: ACETYLATION

<400> SEQUENCE: 6

Gly Gly Lys Ala Pro Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: ACETYLATION

<400> SEQUENCE: 7

Thr Gly Gly Lys Ala Pro Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Peptide substrate corresponding to H3 sequence
      surrounding Lys-14
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: ACETYLATION

<400> SEQUENCE: 8

Ser Thr Gly Gly Lys Ala Pro Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: ACETYLATION

<400> SEQUENCE: 9

Gly Gly Lys Ala Pro Arg Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: ACETYLATION

<400> SEQUENCE: 10

Gly Gly Lys Ala Pro Arg Lys Gln
1               5

<210> SEQ ID NO 11
<211> LENGTH: 8
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: ACETYLATION

<400> SEQUENCE: 11

Lys Ser Thr Gly Gly Lys Ala Pro
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: Peptide substrate corresponding to H3 sequence
      surrounding Lys-14
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: ACETYLATION

<400> SEQUENCE: 12

Thr Gly Gly Lys Ala Pro Arg Lys
1               5

<210> SEQ ID NO 13
<211> LENGTH: 5
<212> TYPE: PRT
<213> ORGANISM: Artificial Sequence
<220> FEATURE:
<223> OTHER INFORMATION: SIRT1 peptide library hit
<220> FEATURE:
<221> NAME/KEY: MOD_RES
<222> LOCATION: (3)..(3)
<223> OTHER INFORMATION: ACETYLATION

<400> SEQUENCE: 13

Gln Pro Lys Gln Ile
1               5

<210> SEQ ID NO 14
<211> LENGTH: 5
<212> TYPE: PRT
<213> ORGANISM: Artificial Sequence
<220> FEATURE:
<223> OTHER INFORMATION: SIRT1 peptide library hit
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (3)..(3)
<223> OTHER INFORMATION: ACETYLATION

<400> SEQUENCE: 14

Arg Pro Lys Gln Phe
1               5

<210> SEQ ID NO 15
<211> LENGTH: 5
<212> TYPE: PRT
<213> ORGANISM: Artificial Sequence
<220> FEATURE:
<223> OTHER INFORMATION: SIRT1 peptide library hit
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (3)..(3)
<223> OTHER INFORMATION: ACETYLATION

<400> SEQUENCE: 15
```

```
Arg Pro Lys Ser Ile
1               5

<210> SEQ ID NO 16
<211> LENGTH: 5
<212> TYPE: PRT
<213> ORGANISM: Artificial Sequence
<220> FEATURE:
<223> OTHER INFORMATION: SIRT1 peptide library hit
<220> FEATURE:
<221> NAME/KEY: MOD_RES
<222> LOCATION: (3)..(3)
<223> OTHER INFORMATION: ACETYLATION

<400> SEQUENCE: 16

Asn His Lys Ile Ile
1               5

<210> SEQ ID NO 17
<211> LENGTH: 5
<212> TYPE: PRT
<213> ORGANISM: Artificial Sequence
<220> FEATURE:
<223> OTHER INFORMATION: SIRT1 peptide library hit
<220> FEATURE:
<221> NAME/KEY: MOD_RES
<222> LOCATION: (3)..(3)
<223> OTHER INFORMATION: ACETYLATION

<400> SEQUENCE: 17

Trp His Lys Phe Gln
1               5

<210> SEQ ID NO 18
<211> LENGTH: 5
<212> TYPE: PRT
<213> ORGANISM: Artificial Sequence
<220> FEATURE:
<223> OTHER INFORMATION: SIRT1 peptide library hit
<220> FEATURE:
<221> NAME/KEY: MOD_RES
<222> LOCATION: (3)..(3)
<223> OTHER INFORMATION: ACETYLATION

<400> SEQUENCE: 18

Val Gln Lys Ile Ile
1               5

<210> SEQ ID NO 19
<211> LENGTH: 5
<212> TYPE: PRT
<213> ORGANISM: Artificial Sequence
<220> FEATURE:
<223> OTHER INFORMATION: SIRT1 peptide library non-hit
<220> FEATURE:
<221> NAME/KEY: MOD_RES
<222> LOCATION: (3)..(3)
<223> OTHER INFORMATION: ACETYLATION

<400> SEQUENCE: 19

Ala Tyr Lys Glu Val
1               5

<210> SEQ ID NO 20
<211> LENGTH: 5
<212> TYPE: PRT
<213> ORGANISM: Artificial Sequence
<220> FEATURE:
<223> OTHER INFORMATION: SIRT1 peptide library non-hit
<220> FEATURE:
```

```
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: ACETYLATION

<400> SEQUENCE: 20

Gln Leu Lys Gly Phe
1               5

<210> SEQ ID NO 21
<211> LENGTH: 5
<212> TYPE: PRT
<213> ORGANISM: Artificial Sequence
<220> FEATURE:
<223> OTHER INFORMATION: SIRT1 peptide library non-hit
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: ACETYLATION

<400> SEQUENCE: 21

Leu Leu Lys Val Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Peptide sequence used for comparison
<220> FEATURE:
<221> NAME/KEY: MOD_RES
<222> LOCATION: (3)..(3)
<223> OTHER INFORMATION: ACETYLATION

<400> SEQUENCE: 22

Trp His Lys Gln Gln
1               5

<210> SEQ ID NO 23
<211> LENGTH: 5
<212> TYPE: PRT
<213> ORGANISM: Artificial Sequence
<220> FEATURE:
<223> OTHER INFORMATION: Peptide sequence used for comparison
<220> FEATURE:
<221> NAME/KEY: MOD_RES
<222> LOCATION: (3)..(3)
<223> OTHER INFORMATION: ACETYLATION

<400> SEQUENCE: 23

Trp Pro Lys Gln Gln
1               5

<210> SEQ ID NO 24
<211> LENGTH: 5
<212> TYPE: PRT
<213> ORGANISM: Artificial Sequence
<220> FEATURE:
<223> OTHER INFORMATION: Peptide sequence used for comparison
<220> FEATURE:
<221> NAME/KEY: MOD_RES
<222> LOCATION: (3)..(3)
<223> OTHER INFORMATION: ACETYLATION
```

```
<400> SEQUENCE: 24

Glu Leu Lys Ala Ser
1               5

<210> SEQ ID NO 25
<211> LENGTH: 5
<212> TYPE: PRT
<213> ORGANISM: Artificial Sequence
<220> FEATURE:
<223> OTHER INFORMATION: Peptide sequence used for comparison
<220> FEATURE:
<221> NAME/KEY: MOD_RES
<222> LOCATION: (3)..(3)
<223> OTHER INFORMATION: ACETYLATION

<400> SEQUENCE: 25

His Lys Lys Leu Met
1               5

<210> SEQ ID NO 26
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 26

Leu Asn Lys Asp Gln
1               5

<210> SEQ ID NO 27
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 27

Trp His Lys Phe Gln
1               5

<210> SEQ ID NO 28
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 28

Trp His Lys Phe Glu
1               5

<210> SEQ ID NO 29
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 29

Ser Tyr Lys Gln Trp
1               5

<210> SEQ ID NO 30
<211> LENGTH: 5
<212> TYPE: PRT
```

```
<213> ORGANISM: Artificial Sequence
<220> FEATURE:
<223> OTHER INFORMATION: SIRT1 hit sequence

<400> SEQUENCE: 30

Gln Pro Lys Gln Ile
1               5

<210> SEQ ID NO 31
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 31

Val Gln Lys Ile Ile
1               5

<210> SEQ ID NO 32
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 32

His Arg Lys Met Pro
1               5

<210> SEQ ID NO 33
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 33

His Lys Lys Met Pro
1               5

<210> SEQ ID NO 34
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 34

Ala Val Lys Phe Met
1               5

<210> SEQ ID NO 35
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 35

Asn His Lys Leu Leu
1               5

<210> SEQ ID NO 36
<211> LENGTH: 5
<212> TYPE: PRT
<213> ORGANISM: Artificial Sequence
```

```
<220> FEATURE:
<223> OTHER INFORMATION: SIRT1 hit sequence

<400> SEQUENCE: 36

Arg Phe Lys Pro Glu
1               5

<210> SEQ ID NO 37
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 37

Lys Phe Lys Pro Glu
1               5

<210> SEQ ID NO 38
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 38

Met Met Lys Gln Gln
1               5

<210> SEQ ID NO 39
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 39

Trp Gly Lys Ser Pro
1               5

<210> SEQ ID NO 40
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 40

Phe Glu Lys Tyr Arg
1               5

<210> SEQ ID NO 41
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 41

Phe Glu Lys Tyr Lys
1               5

<210> SEQ ID NO 42
<211> LENGTH: 5
<212> TYPE: PRT
<213> ORGANISM: Artificial Sequence
<220> FEATURE:
```

```
<223> OTHER INFORMATION: SIRT1 hit sequence

<400> SEQUENCE: 42

Trp Pro Lys Trp Gln
1               5

<210> SEQ ID NO 43
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 43

Arg Ala Lys Met Asp
1               5

<210> SEQ ID NO 44
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 44

Lys Ala Lys Met Asp
1               5

<210> SEQ ID NO 45
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 45

Gly Thr Lys Thr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 46

Gly Tyr Lys Pro Thr
1               5

<210> SEQ ID NO 47
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 47

Ile Phe Lys Thr Phe
1               5

<210> SEQ ID NO 48
<211> LENGTH: 5
<212> TYPE: PRT
<213> ORGANISM: Artificial Sequence
<220> FEATURE:
<223> OTHER INFORMATION: SIRT1 hit sequence
```

```
<400> SEQUENCE: 48

Thr Glu Lys Gln Glu
1               5

<210> SEQ ID NO 49
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 49

His Trp Lys Thr His
1               5

<210> SEQ ID NO 50
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 50

Asp Ser Lys Gly Ala
1               5

<210> SEQ ID NO 51
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 51

Ser Asp Lys Tyr His
1               5

<210> SEQ ID NO 52
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 52

Asn His Lys Ile Ile
1               5

<210> SEQ ID NO 53
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 53

Trp Trp Lys His Gly
1               5

<210> SEQ ID NO 54
<211> LENGTH: 5
<212> TYPE: PRT
<213> ORGANISM: Artificial Sequence
<220> FEATURE:
<223> OTHER INFORMATION: SIRT1 hit sequence
```

```
<400> SEQUENCE: 54

Pro Ile Lys Glu Gln
1               5

<210> SEQ ID NO 55
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 55

Arg Pro Lys Gln Phe
1               5

<210> SEQ ID NO 56
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 56

Lys Pro Lys Gln Phe
1               5

<210> SEQ ID NO 57
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 57

Asp Val Lys Met His
1               5

<210> SEQ ID NO 58
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 58

Ile Tyr Lys Asn Asp
1               5

<210> SEQ ID NO 59
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 59

Thr Pro Lys Asn Ala
1               5

<210> SEQ ID NO 60
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 60
```

Pro Gly Lys Leu Tyr
1               5

<210> SEQ ID NO 61
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 61

Arg Trp Lys Ile Thr
1               5

<210> SEQ ID NO 62
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 62

Lys Trp Lys Ile Thr
1               5

<210> SEQ ID NO 63
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 63

Trp Arg Lys Ile Thr
1               5

<210> SEQ ID NO 64
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 64

Trp Lys Lys Ile Thr
1               5

<210> SEQ ID NO 65
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 65

Trp Pro Lys Ile Thr
1               5

<210> SEQ ID NO 66
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 66

```
Pro Trp Lys Ile Thr
1               5

<210> SEQ ID NO 67
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 67

Arg Pro Lys Ser Ile
1               5

<210> SEQ ID NO 68
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 68

Lys Pro Lys Ser Ile
1               5

<210> SEQ ID NO 69
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 69

Pro Arg Lys Ser Ile
1               5

<210> SEQ ID NO 70
<211> LENGTH: 5
<212> TYPE: PRT
<213> ORGANISM: Artificial Sequence
<220> FEATURE:
<223> OTHER INFORMATION: SIRT1 hit sequence

<400> SEQUENCE: 70

Pro Lys Lys Ser Ile
1               5

<210> SEQ ID NO 71
<211> LENGTH: 24
<212> TYPE: PRT
<213> ORGANISM: Artificial Sequence
<220> FEATURE:
<223> OTHER INFORMATION: H4 histone N-terminal tail library
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa is Ser or pSer
<220> FEATURE:
<221> NAME/KEY: MISC_FEATURE
<222> LOCATION: (3)..(3)
<223> OTHER INFORMATION: Xaa is Arg, MeArg, Me2Arg s,a', or Cit
<220> FEATURE:
<221> NAME/KEY: MISC_FEATURE
<222> LOCATION: (5)..(5)
<223> OTHER INFORMATION: Xaa is Lys or AcLys
<220> FEATURE:
```

```
<221> NAME/KEY: MISC_FEATURE
<222> LOCATION: (8)..(8)
<223> OTHER INFORMATION: Xaa is Lys or AcLys
<220> FEATURE:
<221> NAME/KEY: MISC_FEATURE
<222> LOCATION: (12)..(12)
<223> OTHER INFORMATION: Xaa is Lys or AcLys
<220> FEATURE:
<221> NAME/KEY: MISC_FEATURE
<222> LOCATION: (16)..(16)
<223> OTHER INFORMATION: Xaa is Lys or AcLys
<220> FEATURE:
<221> NAME/KEY: MISC_FEATURE
<222> LOCATION: (20)..(20)
<223> OTHER INFORMATION: Xaa is Lys, AcLys, MeLys, Me2Lys, or Me3Lys
<220> FEATURE:
<221> NAME/KEY: MOD_RES
<222> LOCATION: (22)..(22)
<223> OTHER INFORMATION: bAla
<220> FEATURE:
<221> NAME/KEY: MOD_RES
<222> LOCATION: (23)..(23)
<223> OTHER INFORMATION: bAla

<400> SEQUENCE: 71

Xaa Gly Xaa Gly Xaa Gly Gly Xaa Gly Leu Gly Xaa Gly Gly Ala Xaa
1               5                   10                  15

Arg His Arg Xaa Val Ala Ala Met
            20

<210> SEQ ID NO 72
<211> LENGTH: 5
<212> TYPE: PRT
<213> ORGANISM: Artificial Sequence Sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 72

Trp Xaa Lys Gln Gln
1               5

<210> SEQ ID NO 73
<211> LENGTH: 5
<212> TYPE: PRT
<213> ORGANISM: Artificial Sequence Sequence
<220> FEATURE:
<223> OTHER INFORMATION: Consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 73

Xaa Pro Lys Gln Xaa
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
```

```
<222> LOCATION: (3)..(4)
<223> OTHER INFORMATION: Xaa is beta-Alanine
<220> FEATURE:
<221> NAME/KEY: misc_feature
<222> LOCATION: (5)..(9)
<223> OTHER INFORMATION: Xaa is any naturally occurring amino acid
<220> FEATURE:
<221> NAME/KEY: misc_feature
<222> LOCATION: (7)..(7)
<223> OTHER INFORMATION: Lys is acetylated, a terminal amine or
      biotinylated
<220> FEATURE:
<221> NAME/KEY: misc_feature
<222> LOCATION: (9)..(9)
<223> OTHER INFORMATION: C-terminal Xaa is acetylated

<400> SEQUENCE: 74

Met Arg Xaa Xaa Xaa Xaa Lys Xaa Xaa
1               5
```